United States Patent
Song et al.

(10) Patent No.: US 6,730,481 B2
(45) Date of Patent: May 4, 2004

(54) PRIMERS-ATTACHED VECTOR ELONGATION (PAVE): A 5'-DIRECTED CDNA CLONING STRATEGY

(75) Inventors: Chuanzheng Song, Warren, NJ (US); Julie C. Brown, Melrose, MA (US); Wu Leeying, Somerville, MA (US); Daniel S. Rivera, Concord, MA (US)

(73) Assignee: Genetics Institute, LLC, Cambridge, MA (US)

( * ) Notice: Subject to any disclaimer, the term of this patent is extended or adjusted under 35 U.S.C. 154(b) by 33 days.

(21) Appl. No.: 10/007,357

(22) Filed: Nov. 5, 2001

(65) Prior Publication Data

US 2003/0008298 A1 Jan. 9, 2003

Related U.S. Application Data

(62) Division of application No. 09/527,762, filed on Mar. 17, 2000, now abandoned.
(60) Provisional application No. 60/125,596, filed on Mar. 19, 1999.

(51) Int. Cl.[7] ............................. C12Q 1/68; C12P 19/34; C12N 15/74; C07H 21/04
(52) U.S. Cl. ............................. 435/6; 435/6; 435/320.1; 435/91.1; 536/23.1; 536/24.33
(58) Field of Search ............................. 514/44; 536/23.1, 536/25.4, 22.1, 24.2, 6; 435/91.2, 91.1, 320.1; 935/1, 5, 6, 8, 9, 16, 19, 4; 530/350, 413

(56) References Cited

U.S. PATENT DOCUMENTS 6,022,715 A * 2/2000 Merenkova et al. ........ 435/91.1

OTHER PUBLICATIONS

Boel et al in "A short synthetic adaptor as second–strand primer in the construction of cDNA libraries by the vector–primer method" Biotechniques Jul. 1991;11(1):26, 28.*
Lewis et al in "T4 RNA Ligase: A Molecular Tool for RNA and DNA manipulations" Promega Notes, No. 65, 1998, p. 07.*
D.C. Alexander, et al. "A simplified and efficient vector–primer cDNA cloning system," Gene 31: 79–89 (1984).
G. Bellemare, et al. "High–yield method fir directional cDNA library construction," Gene 98: 231–235 (1991).
P. Carninci, et al. "High–efficiency full–length cDNA cloning by biotinylated CAP trapper," Genomics 37: 327–336 (1996).
P. Carninci, et al. "High efficiency selection of full–length cDNA by improved biotinylated cap trapper," DNA Research 4: 61–66 (1997).
I. Edery, et al. "An efficnet strategy to isolate full–length cDNAs based on an mRNA cap retention procedure (CAPture)," Molecular and Cellular Biology 15(6): 3363–3371 (1995).
A. Efstratiadis, et al. "End labeling of enzymatically decapped mRNA," Nucleic Acids Research 4(12): 4165–4174 (1977).
M. Fromont–Racine, et al. "A highly sensitive method for mapping the 5' termini of mRNAs," Nucleic Acids Research 21(7): 1683–1684 (1993).
S. Kato, et al. "Construction of a human full–length cDNA bank," Gene 150: 243–250 (1994).
X. Liu, et al. "Mapping the 5' and 3' ends of Tetrahymena thermophila mRNAs using RNA ligase mediated amplification of cDNA ends (RLM–RACE)," Nucleic Acids Research 21(21): 4954–4960 (1993).
K. Maruyama & S. Sugano. "Oligo–capping: a simple method to replace the cap structure of eukaryotic mRNAs with oligoribonucleotides," Gene 138: 171–174 (1994).
H. Okayama & P. Berg. "High–efficnecy cloning of full–length cDNA," Molecular and Cellular Biology 2(2): 161–170 (1982).
H. Shinshi, et al. "Enzyme cleaving the 5'–terminal methylated blocked structure of messenger RNA," FEBS Letters 65(2): 254–257 (1976).
H. Shinshi, et al. "A novel phosphodiesterase from cultured tobacco cells," Biochemistry 15(10): 2185–2190 (1976).
M. Soares, et al. "Construction and characterization of a normalized cDNA library," Proc. Natl. Acad. Sci. USA 91: 9228–9232 (1994).
D. Tessier, et al. "Ligation of single–stranted oligodeoxyribonucleotides by T4 RNA ligase," Analytical Biochemistry 158: 171–178 (1986).
M. Yokoyama–Kobayashi & S. Kato. "Recombinant f1 phage particles can transfect monkey COS–7 cells by DEAE dextran method," Biochemical and Biophysical Research Communications 192(2): 935–939 (1993).

* cited by examiner

Primary Examiner—Kenneth R. Horlick
Assistant Examiner—Cynthia Wilder
(74) Attorney, Agent, or Firm—Gavin Bogle

(57) ABSTRACT

A novel method for preparing cDNA libraries is disclosed.

1 Claim, 25 Drawing Sheets

Labeling of Full-length mRNA With An RNA Tag

RNA Tag: BIOTIN-5'-ACUAGUGACCAGCUGAUACGCCUCAAA-3'

The following is the sequence alignment of pED6dpc2 and pED6dpc4.

```
dpc2   1 AAGCTTTTTGCAAAAGCCTAGGCCTCCAAAAAAGCCTCCTCACTACTTCT  50
         ||||||||||||||||||||||||||||||||||||||||||||||||||
dpc4   1 AAGCTTTTTGCAAAAGCCTAGGCCTCCAAAAAAGCCTCCTCACTACTTCT  50

51 GGAATAGCTCAGAGGCCGAGGCGGCCTCGGCCTCTGCATAAATAAAAAAA 100
         ||||||||||||||||||||||||||||||||||||||||||||||||||
      51 GGAATAGCTCAGAGGCCGAGGCGGCCTCGGCCTCTGCATAAATAAAAAAA 100

101 ATTAGTCAGCCATGGGGCGGAGAATGGGCGGAACTGGGCGGAGTTAGGGG 150
         ||||||||||||||||||||||||||||||||||||||||||||||||||
     101 ATTAGTCAGCCATGGGGCGGAGAATGGGCGGAACTGGGCGGAGTTAGGGG 150

151 CGGGATGGGCGGAGTTAGGGGCGGGACTATGGTTGCTGACTAATTGAGAT 200
         ||||||||||||||||||||||||||||||||||||||||||||||||||
     151 CGGGATGGGCGGAGTTAGGGGCGGGACTATGGTTGCTGACTAATTGAGAT 200

201 GCATGCTTTGCATACTTCTGCCTGCTGGGGAGCCTGGGGACTTTCCACAC 250
         ||||||||||||||||||||||||||||||||||||||||||||||||||
     201 GCATGCTTTGCATACTTCTGCCTGCTGGGGAGCCTGGGGACTTTCCACAC 250

251 CTGGTTGCTGACTAATTGAGATGCATGCTTTGCATACTTCTGCCTGCTGG 300
         ||||||||||||||||||||||||||||||||||||||||||||||||||
     251 CTGGTTGCTGACTAATTGAGATGCATGCTTTGCATACTTCTGCCTGCTGG 300

301 GGAGCCTGGGGACTTTCCACACCCTAACTGACACACATTCCACAGGATCC 350
         ||||||||||||||||||||||||||||||||||||||||||||||||||
     301 GGAGCCTGGGGACTTTCCACACCCTAACTGACACACATTCCACAGGATCC 350

351 GGTCGCGCGAATTTCGAGCGGTGTTCCGCGGTCCTCCTCGTATAGAAACT 400
         ||||||||||||||||||||||||||||||||||||||||||||||||||
     351 GGTCGCGCGAATTTCGAGCGGTGTTCCGCGGTCCTCCTCGTATAGAAACT 400

401 CGGACCACTCTGAGACGAAGGCTCGCGTCCAGGCCAGCACGAAGGAGGCT 450
         ||||||||||||||||||||||||||||||||||||||||||||||||||
     401 CGGACCACTCTGAGACGAAGGCTCGCGTCCAGGCCAGCACGAAGGAGGCT 450

451 AAGTGGGAGGGGTAGCGGTCGTTGTCCACTAGGGGGTCCACTCGCTCCAG 500
         ||||||||||||||||||||||||||||||||||||||||||||||||||
     451 AAGTGGGAGGGGTAGCGGTCGTTGTCCACTAGGGGGTCCACTCGCTCCAG 500

501 GGTGTGAAGACACATGTCGCCCTCTTCGGCATCAAGGAAGGTGATTGGTT 550
         ||||||||||||||||||||||||||||||||||||||||||||||||||
     501 GGTGTGAAGACACATGTCGCCCTCTTCGGCATCAAGGAAGGTGATTGGAA 550

551 TATAGGTGTAGGCCACGTGACCGGGTGTTCCTGAAGGGGGGCTATAAAAG 600
         ||||||||||||||||||||||||||||||||||||||||||||||||||
     551 TATAGGTGTAGGCCACGTGACCGGGTGTTCCTGAAGGGGGGCTATAAAAG 600

601 GGGGTGGGGGCGCGTTCGTCCTCACTCTCTTCCGCATCGCTGTCTGCGAG 650
         ||||||||||||||||||||||||||||||||||||||||||||||||||
     601 GGGGTGGGGGCGCGTTCGTCCTCACTCTCTTCCGCATCGCTGTCTGCGAG 650
```

FIG.6A

```
651  GGCCAGCTGTTGGGCTCGCGGTTGAGGACAAACTCTTCGCGGTCTTTCCA 700
     ||||||||||||||||||||||||||||||||||||||||||||||||||
651  GGCCAGCTGTTGGGCTCGCGGTTGAGGACAAACTCTTCGCGGTCTTTCCA 700

701  GTACTCTTGGATCGGAAACCCGTCGGCCTCCGAACGGTACTCCGCCACCG 750
     ||||||||||||||||||||||||||||||||||||||||||||||||||
701  GTACTCTTGGATCGGAAACCCGTCGGCCTCCGAACGGTACTCCGCCACCG 750

751  AGGGACCTGAGCGAGTCCGCATCGACCGGATCGGAAAACCTCTCGACTGT 800
     ||||||||||||||||||||||||||||||||||||||||||||||||||
751  AGGGACCTGAGCGAGTCCGCATCGACCGGATCGGAAAACCTCTCGACTGT 800

801  TGGGGTGAGTACTCCCTCTCAAAAGCGGGCATGACTTCTGCGCTAAGATT 850
     ||||||||||||||||||||||||||||||||||||||||||||||||||
801  TGGGGTGAGTACTCCCTCTCAAAAGCGGGCATGACTTCTGCGCTAAGATT 850

851  GTCAGTTTCCAAAAACGAGGAGGATTTGATATTCACCTGGCCCGCGGTGA 900
     ||||||||||||||||||||||||||||||||||||||||||||||||||
851  GTCAGTTTCCAAAAACGAGGAGGATTTGATATTCACCTGGCCCGCGGTGA 900

901  TGCCTTTGAGGGTGGCCGCGTCCATCTGGTCAGAAAAGACAATCTTTTTG 950
     ||||||||||||||||||||||||||||||||||||||||||||||||||
901  TGCCTTTGAGGGTGGCCGCGTCCATCTGGTCAGAAAAGACAATCTTTTTG 950

951  TTGTCAAGCTTGAGGTGTGGCAGGCTTGAGATCTGGCCATACACTTGAGT 1000
     ||||||||||||||||||||||||||||||||||||||||||||||||||
951  TTGTCAAGCTTGAGGTGTGGCAGGCTTGAGATCTGGCCATACACTTGAGT 1000

1001 GACAATGACATCCACTTTGCCTTTCTCTCCACAGGTGTCCACTCCCAGGT 1050
     ||||||||||||||||||||||||||||||||||||||||||||||||||
1001 GACAATGACATCCACTTTGCCTTTCTCTCCACAGGTGTCCACTCCCAGGT 1050

1051 CCAACTGCA........................Gact 1063
     ||||||||||                        || |
1051 CCAACTGCAGGCCGGCCtctaatacgactcactatagGGCGCGCCtgaat 1100

1064 tcGAATTCt.................................. 1072
     |||| |||
1101 tcGATATCttaagCCCGGGtacGTCGACgcggccgcGCGATCGCccttta 1150

1073 ..........actgaCTCGAGactctattGCGGCCGCaattctaacgtta 1112
         |  ||||||| || |  |||||||||||||||| ||||||
1151 gtgagggTTAATTAActcgagTCTAGAccggGGCCGCaattctaacgtca 1200

1113 ctggccgaagccgcttggaataaggccggtgtgcgtttgtctatatgtta 1162
     ||||||||||||||||||||||||||||||||||||||||||||||||||
1201 ctggccgaagccgcttggaataaggccggtgtgcgtttgtctatatgtta 1250

1163 ttttccaccatattgccgtcttttggcaatgtgagggcccggaaacctgg 1212
     ||||||||||||||||||||||||||||||||||||||||||||||||||
1251 ttttccaccatattgccgtcttttggcaatgtgagggcccggaaacctgg 1300
```

FIG.6B

```
1213 ccctgtcttcttgacgagcattcctaggggtcttccccctctcgccaaag 1262
     ||||||||||||||||||||||||||||||||||||||||||||||||||
1301 ccctgtcttcttgacgagcattcctaggggtcttccccctctcgccaaag 1350

1263 gaatgcaaggtctgttgaatatcgtgaaggaagcagttcctctggaagct 1312
     ||||||||||||||||||||||| ||||||||||||||||||||||||||
1351 gaatgcaaggtctgttgaatgtcgtgaaggaagcagttcctctggaagct 1400

1313 tcttgaagacaaacaacgtctgtagcgaccctttgcaggcagcggaaccc 1362
     ||||||||||||||||||||||||||||||||||||||||||||||||||
1401 tcttgaagacaaacaacgtctgtagcgaccctttgcaggcagcggaaccc 1450

1363 cccacctggcgacaggtgcctctgcggccaaaagccacgtgtataagata 1412
     ||||||||||||||||||||||||||||||||||||||||||||||||||
1451 cccacctggcgacaggtgcctctgcggccaaaagccacgtgtataagata 1500

1413 cacctgcaaaggcggcacaaccccagtgccacgttgtgagttggatagtt 1402
     ||||||||||||||||||||||||||||||||||||||||||||||||||
1501 cacctgcaaaggcggcacaaccccagtgccacgttgtgagttggatagtt 1550

1463 gtggaaagagtcaaatggctctcctcaagcgtattcaacaaggggctgaa 1512
     ||||||||||||||||||||||||||||||||||||||||||||||||||
1551 gtggaaagagtcaaatggctctcctcaagcgtattcaacaaggggctgaa 1600

1513 ggatgcccagaaggtaccccattgtatgggatctgatctggggcctcggt 1562
     ||||||||||||||||||||||||||||||||||||||||||||||||||
1601 ggatgcccagaaggtaccccattgtatgggatctgatctggggcctcggt 1650

1563 gcacatgctttacatgtgtttagtcgaggttaaaaaacgtctaggccccc 1612
     ||||||||||||||||||||||||||||||||||||||||||||||||||
1651 gcacatgctttacatgtgtttagtcgaggttaaaaaacgtctaggccccc 1700

1613 cgaaccacggggacgtggttttcctttgaaaaacacgATgataatattgc 1662
     ||||||||||||||||||||||||||||||||||||||||||||||||||
1701 cgaaccacggggacgtggttttcctttgaaaaacacgATgataatattgc 1750

1663 cacaaccatggttcgaccattgaactgcatcgtcgccgtgtccCAAAATA 1712
     ||||||||||||||||||||||||||||||||||||||||||||||||||
1751 cacaaccatggttcgaccattgaactgcatcgtcgccgtgtccCAAAATA 1800

1713 TGGGGATTGGCAAGAACGGAGACCTACCCTGGCCTCCGCTCAGGAACGAG 1762
     ||||||||||||||||||||||||||||||||||||||||||||||||||
1801 TGGGGATTGGCAAGAACGGAGACCTACCCTGGCCTCCGCTCAGGAACGAG 1850

1763 TTCAAGTACTTCCAAAGAATGaCCACAACCTCTTCAGTGGAAGGTAAACA 1812
     ||||||||||||||||||||| ||||||||||||||||||||||||||||
1851 TTCAAGTACTTCCAAAGAATGACCACAACCTCTTCAGTGGAAGGTAAACA 1900

1813 GAATCTGGTGATTATGGGTAGGAAAACCTGGTTCTCCATTCCTGAGAAGA 1862
     ||||||||||||||||||||||||||||||||||||||||||||||||||
1901 GAATCTGGTGATTATGGGTAGGAAAACCTGGTTCTCCATTCCTGAGAAGA 1950
```

FIG.6C

```
1863 ATCGACCTTTAAAGGACAGAATTAATATAGTTCTCAGTAGAGAACTCAAA 1912
     ||||||||||||||||||||||||||||||||||||||||||||||||||
1951 ATCGACCTTTAAAGGACAGAATTAATATAGTTCTCAGTAGAGAACTCAAA 2000

1913 GAACCACCACGAGGAGCTCATTTTCTTGCCAAAAGTTTGGATGATGCCTT 1962
     ||||||||||||||||||||||||||||||||||||||||||||||||||
2001 GAACCACCACGAGGAGCTCATTTTCTTGCCAAAAGTTTGGATGATGCCTT 2050

1963 AAGACTTATTGAACAACCGGAATTGGCAAGTAAAGTAGACATGGTTTGGA 2012
     ||||||||||||||||||||||||||||||||||||||||||||||||||
2051 AAGACTTATTGAACAACCGGAATTGGCAAGTAAAGTAGACATGGTTTGGA 2100

2013 TAGTCGGAGGCAGTTCTGTTTACCAGGAAGCCATGAATCAACCAGGCCAC 2062
     ||||||||||||||||||||||||||||||||||||||||||||||||||
2101 TAGTCGGAGGCAGTTCTGTTTACCAGGAAGCCATGAATCAACCAGGCCAC 2150

2063 CTCAGACTCTTTGTGACAAGGATCATGCAGGAATTTGAAAGTGACACGTT 2112
     ||||||||||||||||||||||||||||||||||||||||||||||||||
2151 CTCAGACTCTTTGTGACAAGGATCATGCAGGAATTTGAAAGTGACACGTT 2200

2113 TTTCCCAGAAATTGATTTGGGGAAATATAAACTTCTCCCAGAATACCCAG 2162
     ||||||||||||||||||||||||||||||||||||||||||||||||||
2201 TTTCCCAGAAATTGATTTGGCGAAATATAAACTTCTCCCAGAATACCCAG 2250

2163 GCGTCCTCTCTGAGGTCCAGCAGGAAAAAGGCATCAAGTATAAGTTTGAA 2212
     ||||||||||||||||||||||||||||||||||||||||||||||||||
2251 GCGTCCTCTCTGAGGTCCAGGAGGAAAAAGGCATCAAGTATAAGTTTGAA 2300

2213 GTCTACGAGAAGAAAGACTAACAGGAAGATGCTTTCAAGTTCTCTGCTCC 2262
     ||||||||||||||||||||||||||||||||||||||||||||||||||
2301 GTCTACGAGAAGAAAGACTAACAGGAAGATGCTTTCAAGTTCTCTGCTCC 2350

2263 CCTCCTAAAGCTATGCATTTTTTTATAAGACCATGGGACTTTTGCTGGCTT 2312
     ||||||||||||||||||||||||||||||||||||||||||||||||||
2351 CCTCCTAAAGCTATGCATTTTTTTATAAGACCATGGGACTTTTGCTGGCTT 2400

2313 TAGATCATAATCAGCCATACCACATTTGTAGAGGTTTTACTTGCTTTAAA 2362
     ||||||||||||||||||||||||||||||||||||||||||||||||||
2401 TAGATCATAATCAGCCATACCACATTTGTAGAGGTTTTACTTGCTTTAAA 2450

2363 AAACCTCCCACACCTCCCCCTGAACCTGAAACATAAAATGAATGCAATTG 2412
     ||||||||||||||||||||||||||||||||||||||||||||||||||
2451 AAACCTCCCACACCTCCCCCTGAACCTGAAACATAAAATGAATGCAATTG 2500

2413 TTGTTGTTAACTTGTTTATTGCAGCTTATAATGGTTACAAATAAAGCAAT 2462
     ||||||||||||||||||||||||||||||||||||||||||||||||||
2501 TTGTTGTTAACTTGTTTATTGCAGCTTATAATGGTTACAAATAAAGCPAT 2550

2463 AGCATCACAAATTTCACAAATAAAGCATTTTTTTCACTGCATTCTAGTTG 2512
     ||||||||||||||||||||||||||||||||||||||||||||||||||
2551 AGCATCACAAATTTCACAAATAAAGCATTTTTTTCACTGCATTCTAGTTG 2600
```

FIG.6D

```
2513 TGGTTTGTCCAAACTCATCAATGTATCTTATCATGTCTGGATCCCCGGCC 2562
     ||||||||||||||||||||||||||||||||||||||||||||||||||
2601 TGGTTTGTCCAAACTCATCAATGTATCTTATCATGTCTGGATCCCCGGCC 2650

2563 AACGGTCTGGTGACCCGGCTGCGAGAGCTCGGTGTACCTGAGACGCGAGT 2612
     ||||||||||||||||||||||||||||||||||||||||||||||||||
2651 AACGGTCTGGTGACCCGGCTGCGAGAGCTCGGTGTACCTGAGACGCGAGT 2700

2613 AAGCCCTTGAGTCAAAGACGTAGTCGTTGCAAGTCCGCACCAGGTACTGA 2662
     ||||||||||||||||||||||||||||||||||||||||||||||||||
2701 AAGCCCTTGAGTCAAAGACGTAGTCGTTGCAAGTCCGCACCAGGTACTGA 2750

2663 TCATCGATGCTAGACCGTGCAAAAGGAGAGCCTGTAAGCGGGCACTCTTC 2712
     ||||||||||||||||||||||||||||||||||||||||||||||||||
2751 TCATCGATGCTAGACCGTGCAAAAGGAGAGCCTGTAAGCGGGCACTCTTC 2800

2713 CGTGGTCTGGTGGATAAATTCGCAAGGGTATCATGGCGGACGACCGGGGT 2762
     ||||||||||||||||||||||||||||||||||||||||||||||||||
2801 CGTGGTCTGGTGGATAAATTCGCAAGGGTATCATGGCGGACGACCGGGGT 2850

2763 TCGAACCCCGGATCCGGCCGTCCGCCGTGATCCATCCGGTTACCGCCCGC 2812
     ||||||||||||||||||||||||||||||||||||||||||||||||||
2851 TCGAACCCCGGATCCGGCCGTCCGCCGTGATCCATCCGGTTACCGCCCGC 2900

2813 GTGTCGAACCCAGGTGTGCGACGTCAGACAACGGGGGAGCGCTCCTTTTG 2862
     ||||||||||||||||||||||||||||||||||||||||||||||||||
2901 GTGTCGAACCCAGGTGTGCGACGTCAGACAACGGGGGAGCGCTCCTTTTG 2950

2863 GCTTCCTTCCAGGCGCGGCGGCTGCTGCGCTAGCTTTTTTGGCGAGCTCG 2912
     ||||||||||||||||||||||||||||||||||||||||||||||||||
2951 GCTTCCTTCCAGGCGCGGCGGCTGCTGCGCTAGCTTTTTTGGCGAGCTCG 3000

2913 AATTAATTCTGCATTAATGAATCGGCCAACGCGCGGGGAGAGGCGGTTTG 2962
     ||||||||||||||||||||||||||||||||||||||||||||||||||
3001 AATTAATTCTGCATTAATGAATCGGCCAACGCGCGGGGAGAGGCGGTTTG 3050

2963 CGTATTGGGCGCTCTTCCGCTTCCTCGCTCACTGACTCGCTGCGCTCGGT 3012
     ||||||||||||||||||||||||||||||||||||||||||||||||||
3051 CGTATTGGGCGCTCTTCCGCTTCCTCGCTCACTGACTCGCTGCGCTCGGT 3100

3013 CGTTCGGCTGCGGCGAGCGGTATCAGCTCACTCAAAGGCGGTAATACGGT 3062
     ||||||||||||||||||||||||||||||||||||||||||||||||||
3101 CGTTCGGCTGCGGCGAGCGGTATCAGCTCACTCAAAGGCGGTAATACGGT 3150

3063 TATCCACAGAATCAGGGGATAACGCAGGAAAGAACATGTGAGCAAAAGGC 3112
     ||||||||||||||||||||||||||||||||||||||||||||||||||
3151 TATCCACAGAATCAGGGGATAACGCAGGAAAGAACATGTGAGCAAAAGGC 3200

3113 CAGCAAAAGGCCAGGAACCGTAAAAAGGCCGCGTTGCTGGCGTTTTTCCA 3152
     ||||||||||||||||||||||||||||||||||||||||||||||||||
3201 CAGCAAAAGGCCAGGAACCGTAAAAAGGCCGCGTTGCTGGCGTTTTTCCA 3250
```

FIG. 6E

```
3163 TAGGCTCCGCCCCCCTGACGAGCATCACAAAAATCGACGCTCAAGTCAGA 3212
     ||||||||||||||||||||||||||||||||||||||||||||||||||
3251 TAGGCTCCGCCCCCCTGACGAGCATCACAAAAATCGACGCTCAAGTCAGA 3300

3213 GGTGGCGAAACCCGACAGGACTATAAAGATACCAGGCGTTTCCCCCTGGA 3262
     ||||||||||||||||||||||||||||||||||||||||||||||||||
3301 GGTGGCGAAACCCGACAGGACTATAAAGATACCAGGCGTTTCCCCCTGGA 3350

3263 AGCTCCCTCGTGCGCTCTCCTGTTCCGACCCTGCCGCTTACCGGATACCT 3312
     ||||||||||||||||||||||||||||||||||||||||||||||||||
3351 AGCTCCCTCGTGCGCTCTCCTGTTCCGACCCTGCCGCTTACCGGATACCT 3400

3313 GTCCGCCTTTCTCCCTTCGGGAAGCGTGGCGCTTTCTCAATGCTCACGCT 3362
     ||||||||||||||||||||||||||||||||||||||||||||||||||
3401 GTCCGCCTTTCTCCCTTCGGGAAGCGTGGCGCTTTCTCAATGCTCACGCT 3450

3363 GTAGGTATCTCAGTTCGGTGTAGGTCGTTCGCTCCAAGCTGGGCTGTGTG 3412
     ||||||||||||||||||||||||||||||||||||||||||||||||||
3451 GTAGGTATCTCAGTTCGGTGTAGGTCGTTCGCTCCAAGCTGGGCTGTGTG 3500

3413 CACGAACCCCCCGTTCAGCCCGACCGCTGCGCCTTATCCGGTAACTATCG 3462
     ||||||||||||||||||||||||||||||||||||||||||||||||||
3501 CACGAACCCCCCGTTCAGCCCGACCGCTGCGCCTTATCCGGTAACTATCG 3550

3463 TCTTGAGTCCAACCCGGTAAGACACGACTTATCGCCACTGGCAGCAGCCA 3512
     ||||||||||||||||||||||||||||||||||||||||||||||||||
3551 TCTTGAGTCCAACCCGGTAAGACACGACTTATCGCCACTGGCAGCAGCCA 3600

3513 CTGGTAACAGGATTAGCAGAGCGAGGTATGTAGGCGGTGCTACAGAGTTC 3562
     ||||||||||||||||||||||||||||||||||||||||||||||||||
3601 CTGGTAACAGGATTAGCAGAGCGAGGTATGTAGGCGGTGCTACAGAGTTC 3650

3563 TTGAAGTGGTGGCCTAACTACGGCTACACTAGAAGGACAGTATTTGGTAT 3612
     ||||||||||||||||||||||||||||||||||||||||||||||||||
3651 TTGAAGTGGTGGCCTAACTACGGCTACACTAGAAGGACAGTATTTGGTAT 3700

3613 CTGCGCTCTGCTGAAGCCAGTTACCTTCGGAAAAAGAGTTGGTAGCTCTT 3662
     ||||||||||||||||||||||||||||||||||||||||||||||||||
3701 CTGCGCTCTGCTGAAGCCAGTTACCTTCGGAAAAAGAGTTGGTAGCTCTT 3750

3663 GATCCGGCAAACAAACCACCGCTGGTAGCGGTGGTTTTTTTGTTTGCAAG 3712
     ||||||||||||||||||||||||||||||||||||||||||||||||||
3751 GATCCGGCAAACAAACCACCGCTGGTAGCGGTGGTTTTTTTGTTTGCAAG 3800

3713 CAGCAGATTACGCGCAGAAAAAAAGGATCTCAAGAAGATCCTTTGATCTT 3762
     ||||||||||||||||||||||||||||||||||||||||||||||||||
3801 CAGCAGATTACGCGCAGAAAAAAAGGATCTCAAGAAGATCCTTTGATCTT 3850

3763 TTCTACGGGGTCTGACGCTCAGTGGAACGAAAACTCACGTTAAGGGATTT 3812
     ||||||||||||||||||||||||||||||||||||||||||||||||||
3851 TTCTACGGGGTCTGACGCTCAGTGGAACGAAAACTCACGTTAAGGGATTT 3900
```

FIG.6F

```
3813 TGGTCATGAGATTATCAAAAAGGATCTTCACCTAGATCCTTTTAAATTAA 3862
     ||||||||||||||||||||||||||||||||||||||||||||||||||
3901 TGGTCATGAGATTATCAAAAAGGATCTTCACCTAGATCCTTTTAAATTAA 3950

3863 AAATGAAGTTTTAAATCAATCTAAAGTATATATGAGTAAACTTGGTCTGA 3912
     ||||||||||||||||||||||||||||||||||||||||||||||||||
3951 AAATGAAGTTTTAAATCAATCTAAAGTATATATGAGTAAACTTGGTCTGA 4000

3913 CAGTTACCAATGCTTAATCAGTGAGGCACCTATCTCAGCGATCTGTCTAT 3962
     ||||||||||||||||||||||||||||||||||||||||||||||||||
4001 CAGTTACCAATGCTTAATCAGTGAGGCACCTATCTCAGCGATCTGTCTAT 4050

3963 TTCGTTCATCCATAGTTGCCTGACTCCCCGTCGTGTAGATAACTACGATA 4012
     ||||||||||||||||||||||||||||||||||||||||||||||||||
4051 TTCGTTCATCCATAGTTGCCTGACTCCCCGTCGTGTAGATAACTACGATA 4100

4013 CGGGAGGGCTTACCATCTGGCCCCAGTGCTGCAATGATACCGCGAGACCC 4062
     ||||||||||||||||||||||||||||||||||||||||||||||||||
4101 CGGGAGGGCTTACCATCTGGCCCCAGTGCTGCAATGATACCGCGAGACCC 4150

4063 ACGCTCACCGGCTCCAGATTTATCAGCAATAAACCAGCCAGCCGGAAGGG 4112
     ||||||||||||||||||||||||||||||||||||||||||||||||||
4151 ACGCTCACCGGCTCCAGATTTATCAGCAATAAACCAGCCAGCCGGAAGGG 4200

4113 CCGAGCGCAGAAGTGGTCCTGCAACTTTATCCGCCTCCATCCAGTCTATT 4162
     ||||||||||||||||||||||||||||||||||||||||||||||||||
4201 CCGAGCGCAGAAGTGGTCCTGCAACTTTATCCGCCTCCATCCAGTCTATT 4250

4163 AATTGTTGCCGGGAAGCTAGAGTAAGTAGTTCGCCAGTTAATAGTTTGCG 4212
     ||||||||||||||||||||||||||||||||||||||||||||||||||
4251 AATTGTTGCCGGGAAGCTAGAGTAAGTAGTTCGCCAGTTAATAGTTTGCG 4300

4213 CAACGTTGTTGCCATTGCTACAGGCATCGTGGTGTCACGCTCGTCGTTTG 4262
     ||||||||||||||||||||||||||||||||||||||||||||||||||
4301 CAACGTTGTTGCCATTGCTACAGGCATCGTGGTGTCACGCTCGTCGTTTG 4350

4263 GTATGGCTTCATTCAGCTCCGGTTCCCAACGATCAAGGCGAGTTACATGA 4312
     ||||||||||||||||||||||||||||||||||||||||||||||||||
4351 GTATGGCTTCATTCAGCTCCGGTTCCCAACGATCAAGGCGAGTTACATGA 4400

4313 TCCCCCATGTTGTGCAAAAAAGCGGTTAGCTCCTTCGGTCCTCCGATCGT 4362
     ||||||||||||||||||||||||||||||||||||||||||||||||||
4401 TCCCCCATGTTGTGCAAAAAAGCGGTTAGCTCCTTCGGTCCTCCGATCGT 4450

4363 TGTCAGAAGTAAGTTGGCCGCAGTGTTATCACTCATGGTTATGGCAGCAC 4412
     ||||||||||||||||||||||||||||||||||||||||||||||||||
4451 TGTCAGAAGTAAGTTGGCCGCAGTGTTATCACTCATGGTTATGGCAGCAC 4500

4413 TGCATAATTCTCTTACTGTCATGCCATCCGTAAGATGCTTTTCTGTGACT 4462
     ||||||||||||||||||||||||||||||||||||||||||||||||||
4501 TGCATAATTCTCTTACTGTCATGCCATCCGTAAGATGCTTTTCTGTGACT 4550
```

FIG.6G

```
4463 GGTGAGTACTCAACCAAGTCATTCTGAGAATAGTGTATGCGGCGACCGAG 4512
     ||||||||||||||||||||||||||||||||||||||||||||||||||
4551 GGTGAGTACTCAACCAAGTCATTCTGAGAATAGTGTATGCGGCGACCGAG 4600

4513 TTGCTCTTGCCCGGCGTCAATACGGGATAATACCGCGCCACATAGCAGAA 4562
     ||||||||||||||||||||||||||||||||||||||||||||||||||
4601 TTGCTCTTGCCCGGCGTCAATACGGGATAATACCGCGCCACATAGCAGAA 4650

4563 CTTTAAAAGTGCTCATCATTGGAAAACGTTCTTCGGGGCGAAAACTCTCA 4612
     ||||||||||||||||||||||||||||||||||||||||||||||||||
4651 CTTTAAAAGTGCTCATCATTGGAAAACGTTCTTCGGGGCGAAAACTCTCA 4700

4613 AGGATCTTACCGCTGTTGAGATCCAGTTCGATGTAACCCACTCGTGCACC 4662
     ||||||||||||||||||||||||||||||||||||||||||||||||||
4701 AGGATCTTACCGCTGTTGAGATCCAGTTCGATGTAACCCACTCGTGCACC 4750

4663 CAACTGATCTTCAGCATCTTTTACTTTCACCAGCGTTTCTGGGTGAGCAA 4712
     ||||||||||||||||||||||||||||||||||||||||||||||||||
4751 CAACTGATCTTCAGCATCTTTTACTTTCACCAGCGTTTCTGGGTGAGCAA 4800

4713 AAACAGGAAGGCAAAATGCCGCAAAAAAGGGAATAAGGGCGACACGGAAA 4762
     ||||||||||||||||||||||||||||||||||||||||||||||||||
4801 AAACAGGAAGGCAAAATGCCGCAAAAAAGGGAATAAGGGCGACACGGAAA 4850

4763 TGTTGAATACTCATACTCTTCCTTTTTCAATATTATTGAAGCATTTATCA 4812
     ||||||||||||||||||||||||||||||||||||||||||||||||||
4851 TGTTGAATACTCATACTCTTCCTTTTTCAATATTATTGAAGCATTTATCA 4900

4813 GGGTTATTGTCTCATGAGCGGATACATATTTGAATGTATTTAGAAAAATA 4862
     ||||||||||||||||||||||||||||||||||||||||||||||||||
4901 GGGTTATTGTCTCATGAGCGGATACATATTTGAATGTATTTAGAAAAATA 4950

4863 AACAAATAGGGGTTCCGCGCACATTTCCCCGAAAAGTGCCACCTGACGTC 4912
     ||||||||||||||||||||||||||||||||||||||||||||||||||
4951 AACAAATAGGGGTTCCGCGCACATTTCCCCGAAAAGTGCCACCTGACGTC 5000

4913 TAAGAAACCATTATTATCATGACATTAACCTATAAAAATAGGCGTATCAC 4962
     ||||||||||||||||||||||||||||||||||||||||||||||||||
5001 TAAGAAACCATTATTATCATGACATTAACCTATAAAAATAGGCGTATCAC 5050

4963 GAGGCCCTTTCGTCTCGCGCGTTTCGGTGATGACGGTGAAAACCTCTGAC 5012
     ||||||||||||||||||||||||||||||||||||||||||||||||||
5051 GAGGCCCTTTCGTCTCGCGCGTTTCGGTGATGACGGTGAAAACCTCTGAC 5100

5013 ACATGCAGCTCCCGGAGACGGTCACAGCTTGTCTGTAAGCGGATGCCGGG 5062
     ||||||||||||||||||||||||||||||||||||||||||||||||||
5101 ACATGCAGCTCCCGGAGACGGTCACAGCTTGTCTGTAAGCGGATGCCGGG 5150

5063 AGCAGACAAGCCCGTCAGGGCGCGTCAGCGGGTGTTGGCGGGTGTCGGGG 5112
     ||||||||||||||||||||||||||||||||||||||||||||||||||
5151 AGCAGACAAGCCCGTCAGGGCGCGTCAGCGGGTGTTGGCGGGTGTCGGGG 5200
```

FIG.6H

```
5113 CTGGCTTAACTATGCGGCATCAGAGCAGATTGTACTGAGAGTGCACCATA 5162
     ||||||||||||||||||||||||||||||||||||||||||||||||||
5201 CTGGCTTAACTATGCGGCATCAGAGCAGATTGTACTGAGAGTGCACCATA 5250

5163 TGCGGTGTGAAATACCGCACAGATGCGTAAGGAGAAAATACCGCATCAGG 5212
     ||||||||||||||||||||||||||||||||||||||||||||||||||
5251 TGCGGTGTGAAATACCGCACAGATGCGTAAGGAGAAAATACCGCATCAGG 5300

5213 CGCCATTCGCCATTCAGGCTGCGCAACTGTTGGGAAGGGCGATCGGTGCG 5262
     ||||||||||||||||||||||||||||||||||||||||||||||||||
5301 CGCCATTCGCCATTCAGGCTGCGCAACTGTTGGGAAGGGCGATCGGTGCG 5350

5263 GGCCTCTTCGCTATTACGCCAGCTGGCGAAAGGGGGATGTGCTGCAAGGC 5312
     ||||||||||||||||||||||||||||||||||||||||||||||||||
5351 GGCCTCTTCGCTATTACGCCAGCTGGCGAAAGGGGGATGTGCTGCAAGGC 5400

5313 GATTAAGTTGGGTAACGCCAGGGTTTTCCCAGTCACGACGTTGTAAAACG 5362
     ||||||||||||||||||||||||||||||||||||||||||||||||||
5401 GATTAAGTTGGGTAACGCCAGGGTTTTCCCAGTCACGACGTTGTAAAACG 5450

5363 ACGGCCAGTGCC 5374
     ||||||||||||
5451 ACGGCCAGTGCC 5462
```

FIG.6I

Preparation of Primers-Attached-Vector

Plasmid name: pNOTs
Plasmid size: 4529 bp

Comments/References: pNOTs is a derivative of pMT2 (Kaufman et al, 1989. Mol.Cell. Biol.9:946-958). DHFR was deleted and a new polylinker was inserted between EcoRI and HpaI. M13 origin of replication was inswerted in the ClaI site. SST cDNAs are cloned between EcoRI and NotI.

cDNA Synthesis and Cloning: PAVE

PRIMERS-ATTACHED VECTOR ELONGATION (PAVE): A 5'-DIRECTED CDNA CLONING STRATEGY

This is a divisional of application Ser. No. 09/527,762 filed on Mar. 17, 2000, now abandoned, the entire disclosure of which is hereby incorporated by reference, and claims the benefit of U.S. Provisional Application No. 60/125,596, filed on March 19, 1999.

FIELD OF THE INVENTION

The present invention provides a novel method for preparing cDNA libraries containing enhanced percentages of full-length cDNA inserts.

BACKGROUND OF THE INVENTION

Technology aimed at the production of cDNA libraries, which are important tools in the discovery of biologically relevant genetic sequences, often produces cDNA libraries that are far from perfect. cDNA libraries may contain a high percentage of molecules where the cDNA insert within the library vector is not full-length as compared to the naturally-occurring mRNA molecule from which the cDNA was derived. cDNA libraries, even those designed to be "directional" or having the cDNA insert present in a particular 5'→>3' orientation relative to the vector sequences, often contain a high percentage of "flipped" inserts where the cDNA insert is oriented in the opposite orientation from that which is most desirable for characterization and expression of the cDNA insert. In addition, some cDNA libraries demonstrate a high incidence of multiple inserts, where unrelated cDNA molecules are aberrantly ligated into the same vector molecule.

There exists a need for novel methods of cDNA library production, and it is to such methods that the present invention is directed.

Construction of high quality cDNA libraries, with greater than 90% of the inserts being the full-length copy of the corresponding mRNA molecules, is crucial to the success of our effort to clone all the human genes encoding secreted proteins. Several factors contribute to the poor quality of cDNA libraries constructed using the conventional method, i.e., cDNA synthesis followed by ligation into plasmid or phage vectors. First, mRNA molecules may be degraded during RNA isolation and in the process of first strand cDNA synthesis. In addition, most mRNA samples are isolated from total cellular RNA using the oligo-dT capture protocol and, therefore, contaminated with partially-precessed poly (A) containing precursor RNA and partially degraded 3' portion of mRNA molecules. Second, during first-strand cDNA synthesis, reverse transcriptase tends to prematurely fall off the RNA templates due to RNA secondary structures or insufficient processivity of the enzyme itself. Third, the ligation step after ds cDNA synthesis may result in the following undesirable artifacts: A). Multiple cDNA inserts are ligated into the same vector due to the high insert/vector ratio used to increase the population of clones containing a cDNA insert. B). There is a high percentage (about 10%) of flipped cDNA insert when a unidirectional library is constructed. C). Contaminating DNA can be incorporated into the library. For example, some of the early libraries constructed by Clontech were contaminated by yeast chromosome DNA when yeast tRNA was used to precipitated the cDNA. Another example is that when the full-length cDNA was selected (Carninci, et al., 1996), ligation of contaminating partial cDNA into the vector compromised the quality of library. D). There is a selection for smaller cDNA inserts since they are ligated more efficiently than larger ones.

Numerous efforts have been taken to increase the cloning efficiency from a definite amount of mRNA and/or to increase the proportion of the full-length inserts. Some of the most successful approaches include: A). An engineered reverse transcriptase was designed by GIBCO-BRL to inactivate its Rnase H activity, which causes on-template RNA cleavage and premature termination of transcription when the enzyme stutters before a secondary structure. Thus far, the Superscript II reverse transcriptase (BRL) remains the most popular enzyme for first-strand cDNA synthesis. B). Oligo-dT tailed vectors were used for first-strand cDNA synthesis (Okayama and Berg, 1982); Alexander et al., 1984; Bellemare et al., 1991; Kato et al., 1994). This method dramatically increased the cloning efficiency and the proportion of insert-containing clones. C). Strategies for specific capture (Edery et al., 1995) or labeling of the 5'-end cap of mRNA molecules with oligonucleotides (Fromont-Racine et al., 1993; Liu and Gorovsky, 1993; Maruyama and Sugano, 1994; Kato et al., 1994) or biotin (Carninci et al., 1996, 1997) were used to select for full-length cDNA. Libraries constructed with a selection for the 5'-end cap such as the Kato strategy (Kato et al., 1994, the Protagene protocol) and the biotin capture method (Carcinci et al., 1996) have a high percentage of full-length cDNA inserts ranging from 70% to 95%. However, none of the above mentioned strategies could completely satisfy the requirements for high efficiency, high proportion of full-length cDNA inserts and low contaminating or aberrant DNA inserts due to DNA ligation.

The origin, function, and position of the various elements of the pED6pdpc2 expression plasmid are provided below. The various nucleotide (nt) positions within the plasmid are given relative to the 5' end of the SV40 enhancer segment, the first nt of which was assigned as Position 1. DiscoverEase™ cDNAs are cloned between EcoRI and NotI. CiaI, NheI, SapI, and NdeI are unique sites in the, expression plasmid.

Sv40 enhancer (nt 1–345): This fragment originated from the SV40 genome. It contains the SV40 origin of replication and transcriptional enhancer. The SV40 enhancer sequence increases the level of transcription from the adenovirus 2 (Ad2) major late promoter.

Ad2 MLP (nt 364–656): This fragment contains the Ad2 major late promoter (MLP) from XhoI to PvuII.

Ad2 TPL (nt 657–796): This fragment represents a cDNA copy of the majority of the tripartite leader present on all late Ad2 mRNAs. Hybrid intron (nt 797–1059): The hybrid intervening sequence contains a 5' splice from the Adenovirus tripartite leader and a 3' splice from a murine IgG gene.

Polylinker (nt 1059–1093): The DiscoverEase™ cDNAs are cloned into the EcoRI-NotI site. The 5' end of the cDNAs contains a SfiI site.

EMCV Leader (nt 1104–1649): This sequence is derived from the encephalomyocarditis virus (EMCV) RNA. This sequence allows ribosomes to initiate translation internally, resulting in a more efficient translation of the DHFR gene.

Mouse DHFR cDNA (nt 1650–2317): A selectable marker in Chinese hamster ovary cells.

SV40 polyadenylation site (nt 2318–2550): This fragment contains the polyadenylation site from the SV40 early region.

Ad2 VAI gene (nt 2551–2905): This fragment is derived from the Ad2 genome and encodes the virus-associated RNA I.

pUC 19 backbone (nt 2906–5374): This fragment includes the CoI EI origin of replication which allows replication of the plasmid in *E. coli*, and the beta-lactamase gene (nt 3913–4708) which confers ampicillin resistance and is used as a selectable marker in the propagation of the plasmid in *E. coli*.

FIG. 6 is a nucleotide sequence alignment that shows in detail the nucleotide differences between the pED6pdc2 (SEQ ID NO: 7) and pED6pdc4 (SEQ ID NO: 6) vectors.

Figure 7:
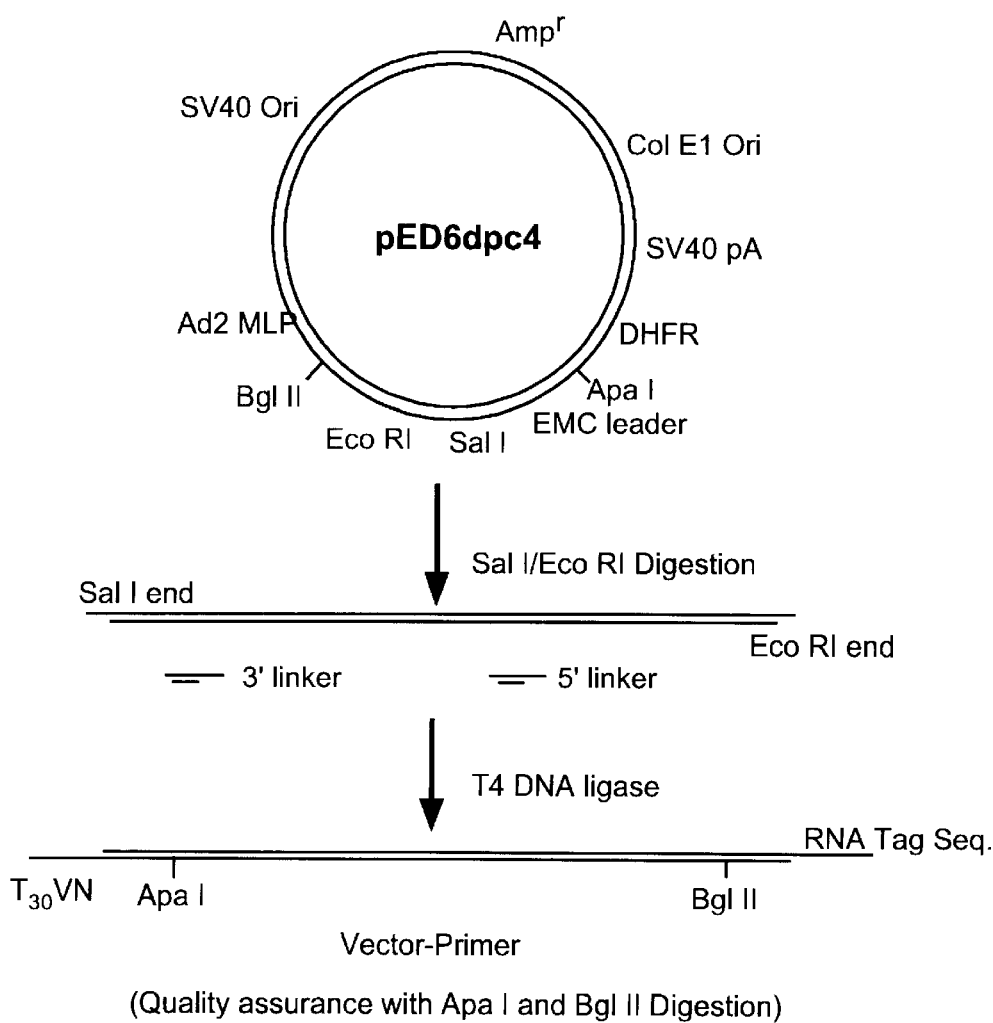

FIG. 7 is a schematic representation of the pED6pdc4 vector that may be used for construction of cDNA libraries as disclosed herein, and shows that the vector is digested with certain restriction enzymes and ligated to particular 5' and 3' linkers to form a pED6pdc4 vector-primer construct. The 5' linker that starts in the 5' direction is SEQ ID NO: 13. The 5' linker that starts in the 3' direction is SEQ ID NO: 2. The 3' linker that starts in the 5' direction is SEQ ID NO: 3. The 3' linker that starts in the 3' direction is SEQ ID NO: 11.

Figure 8:
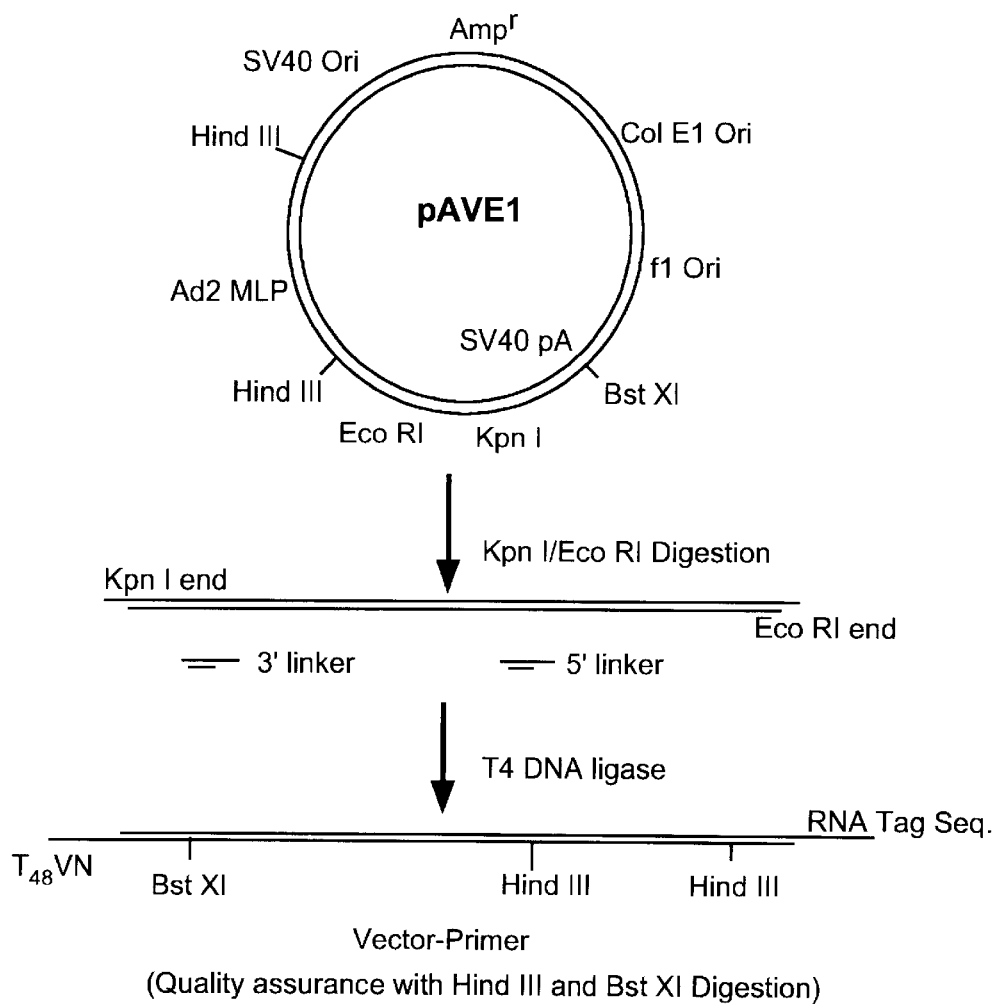

FIG. 8 is a schematic representation of the pAVE1 vector that may be used for construction of cDNA libraries as disclosed herein, and shows that the vector is digested with certain restriction enzymes and ligated to particular 5' and 3' linkers to form a pAVE1 vector-primer construct. The 5' linker in the 5' direction is SEQ ID NO: 13. The 5' linker in the 3' direction is SEQ ID NO: 2. The 3' linker in the 5' direction is SEQ ID NO: 3. The 3' linker in the 3' direction is SEQ ID NO: 12.

Figure 9:
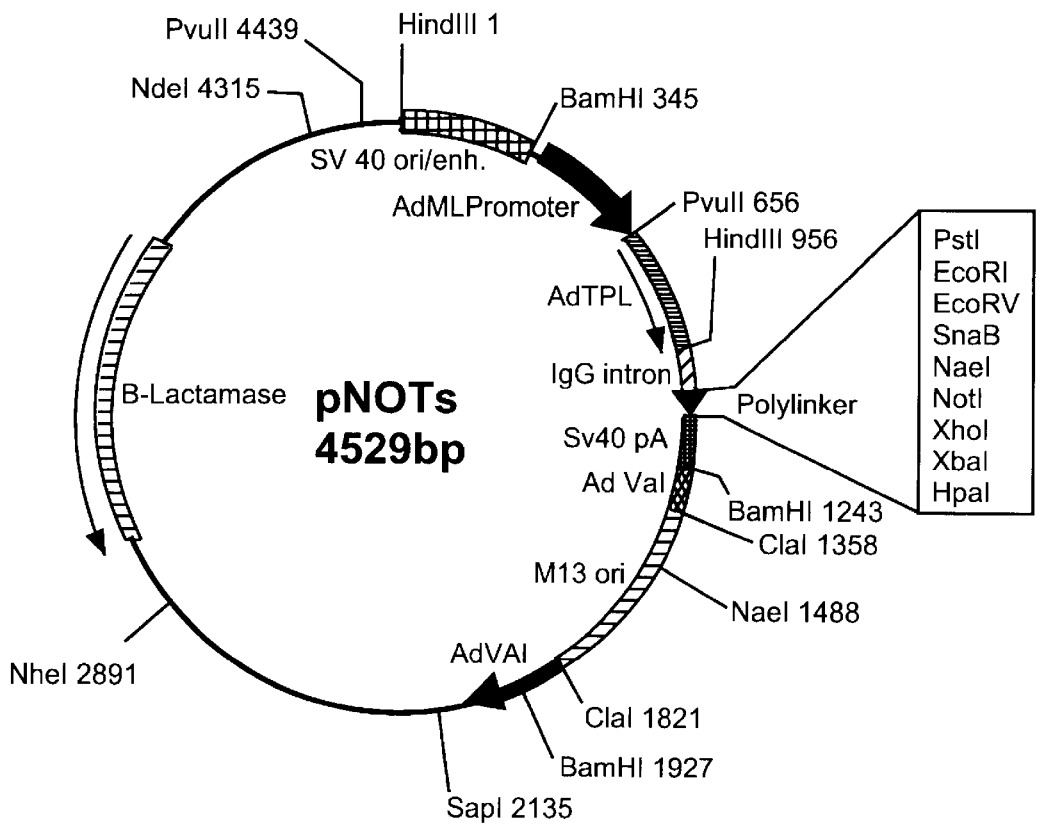

FIG. 9 is a schematic representation of the pNOTs vector from which the pAVE1 vector was derived. The pNOTs vector was derived from pMT2 (Kaufman et al., 1989, *Mol.*

*Cell. Biol.* 9: 946–958) by deletion of the DHFR sequences, insertion of a new polylinker, and insertion of the M13 origin of replication in the ClaI site.

Figure 10:
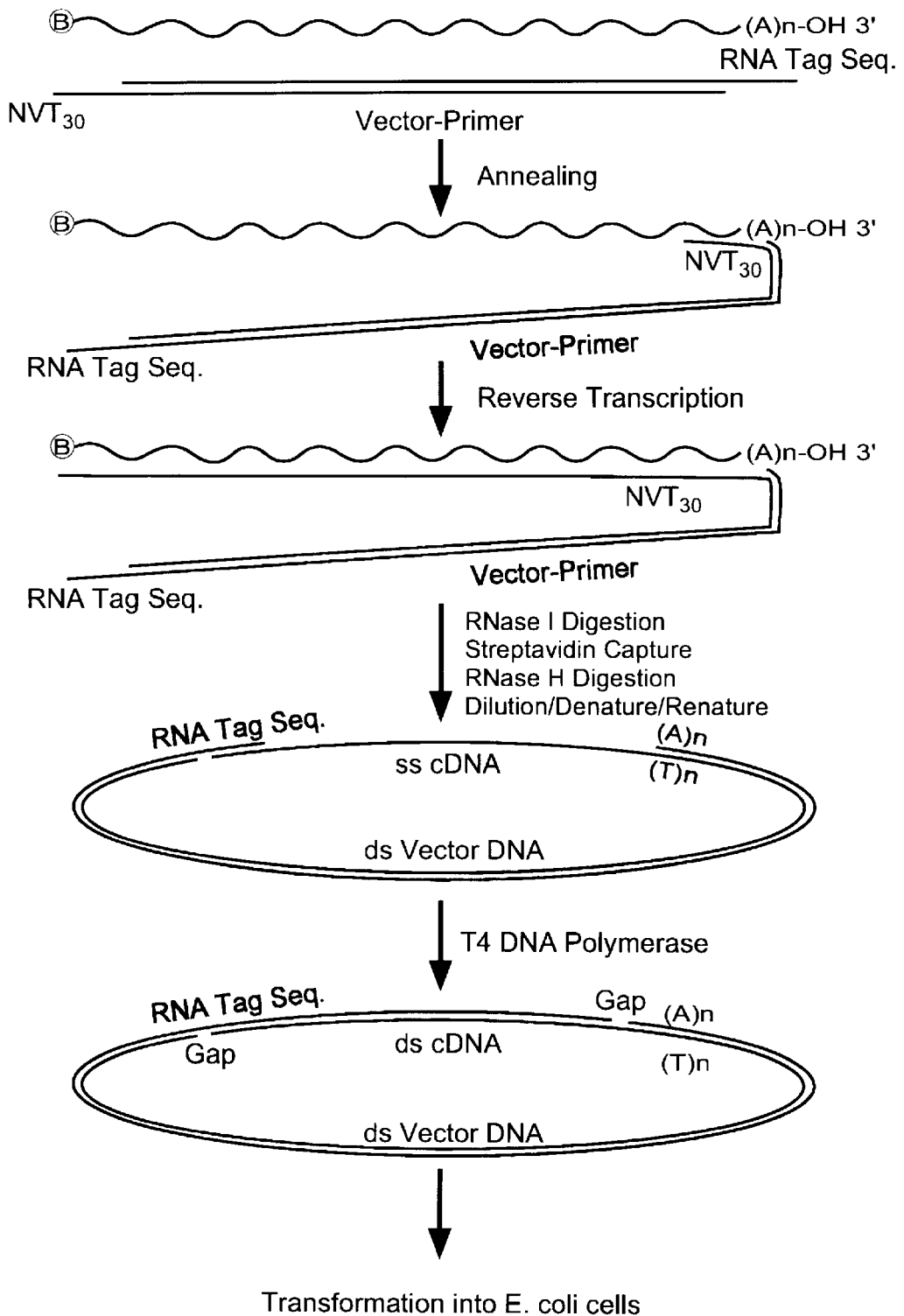

FIG. 10 is a schematic representation showing the creation of cDNA libraries by the combination of RNA-tagged mRNA molecules and pED6pdc4 vector-primer construct molecules, followed by first-strand synthesis (annealing and elongation by reverse transcriptase), RNAse digestion, intramolecular renaturation, and second-strand synthesis.

Figure 11:
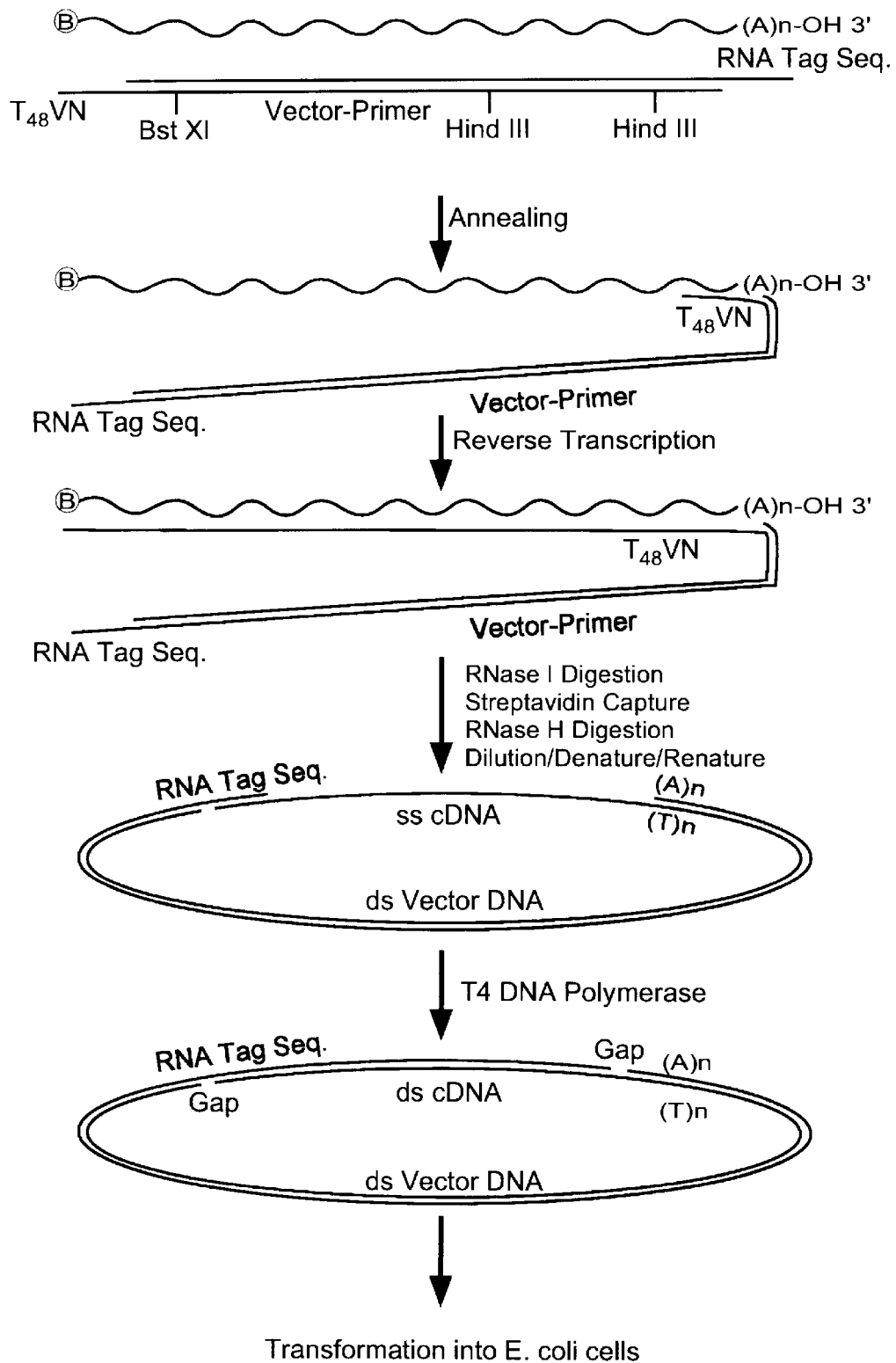

FIG. 11 is a schematic representation showing the creation of cDNA libraries by the combination of RNA-tagged mRNA molecules and pAVE1 vector-primer construct molecules, followed by first-strand synthesis (annealing and elongation by reverse transcriptase), RNAse digestion, intramolecular renaturation, and second-strand synthesis. Note that in this figure the sequence at the 3' end of the Vector-Primer construct has been reversed: the 3' should be shown as $NV(T)_{48}$ as in the 3' linker shown in FIG. 8.

Figure 12:
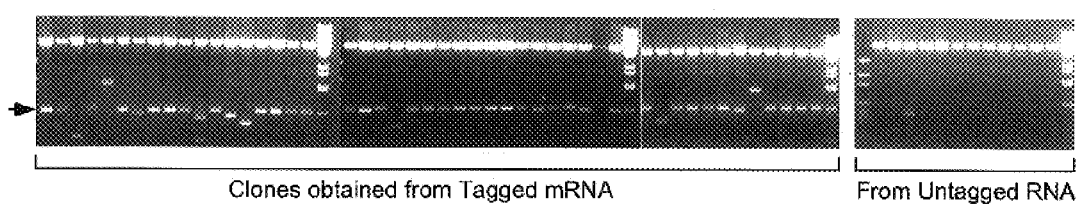

FIG. 12 is an agarose gel of digested cDNA clones showing the results of using the Primers-Attached Vector Elongation (PAVE) strategy with RNA-tagged globin mRNA: approximately 80% of the globin cDNAs are the expected size for full-length cDNA inserts (arrow), while for the untagged RNA controls full-length cDNA inserts are present at a much lower frequency.

Figure 13:
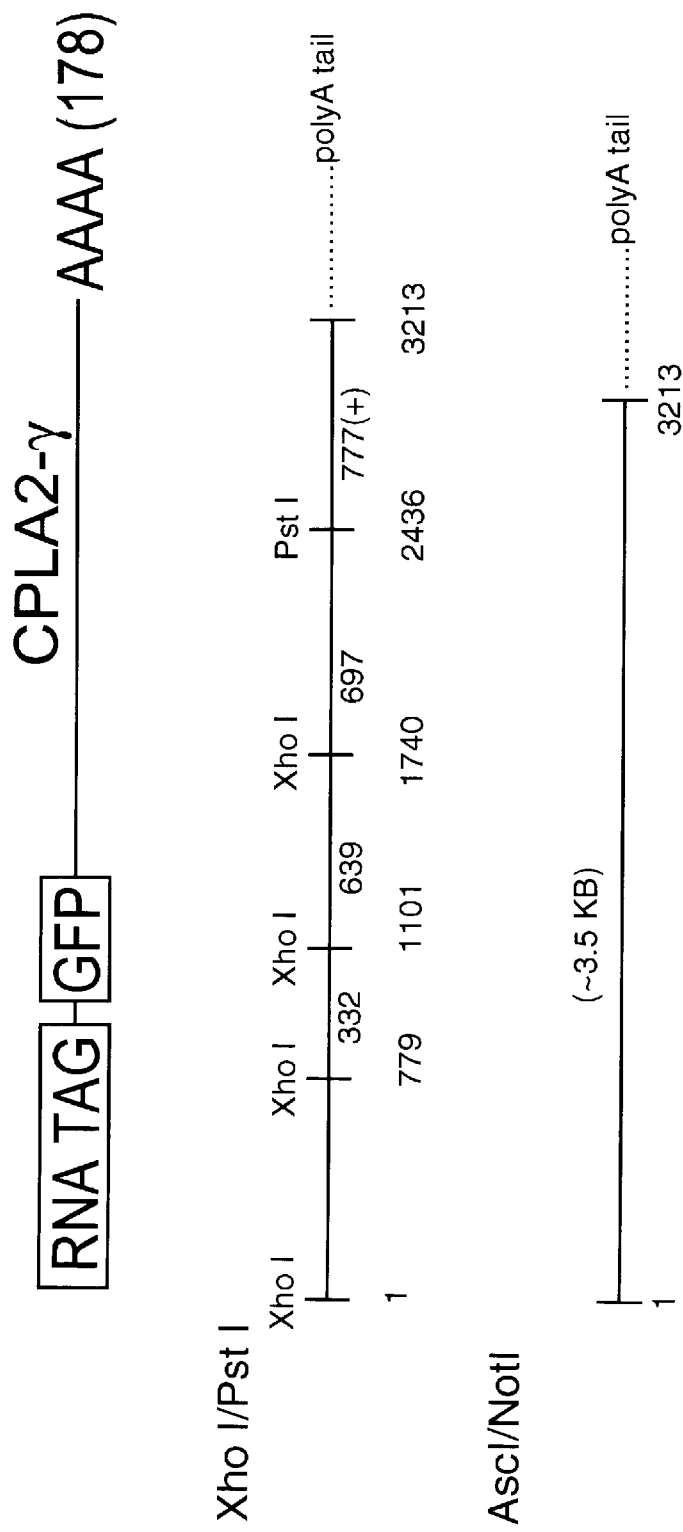

FIG. 13 shows schematically the structure of an RNA-tagged CPLA2-γ mRNA molecule used in the experiments of FIGS. 13–17.

Figure 14:
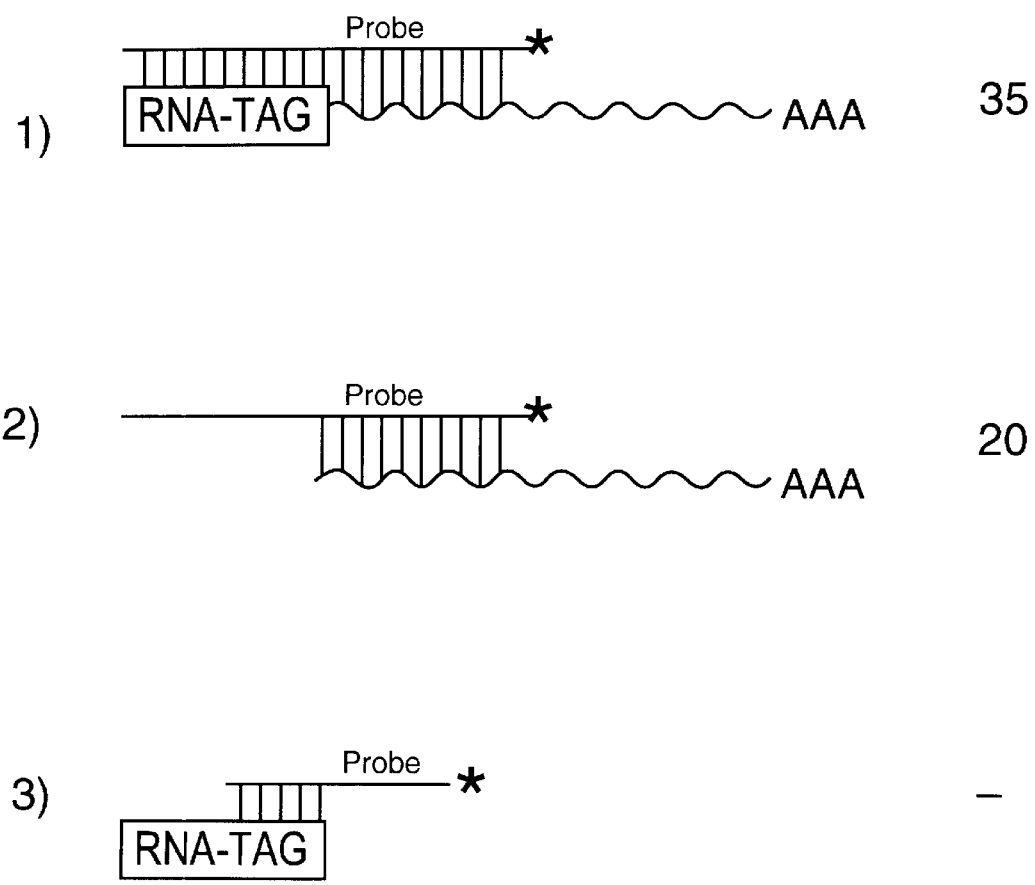

FIG. 14 shows schematically the structures and predicted sizes (as number of nucleotide residues) of different probe-RNA hybrids that could result from RNA-RNA ligation followed by RNAse digestion to remove single-stranded RNA.

Figure 15:
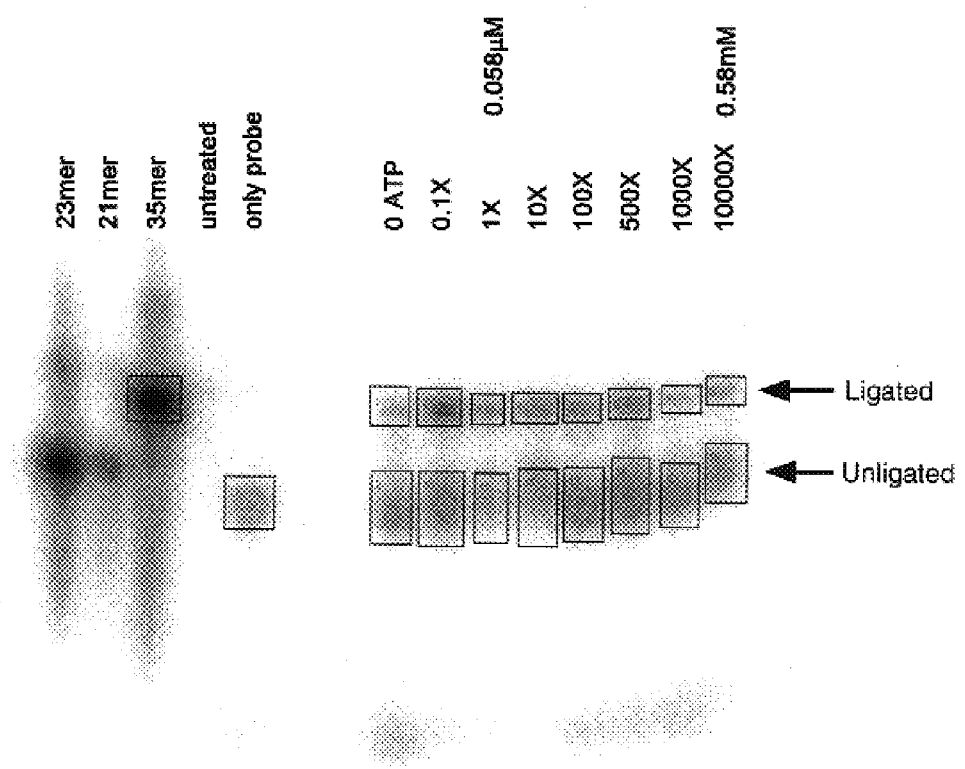

FIG. 15 is a digitized scan of radioactively detected RNA molecules separated electrophoretically on a gel, showing the effect of ATP concentration upon the efficiency of the reaction adding a RNA tag to a mRNA molecule using T4 RNA ligase. Arrows show the expected sizes for ligated and unligated molecules. At a relative concentration of 0.1×(5.8 nM ATP), 50.8 percent of the radioactivity detected was present as ligated molecules as compared to unligated molecules.

Figure 16:
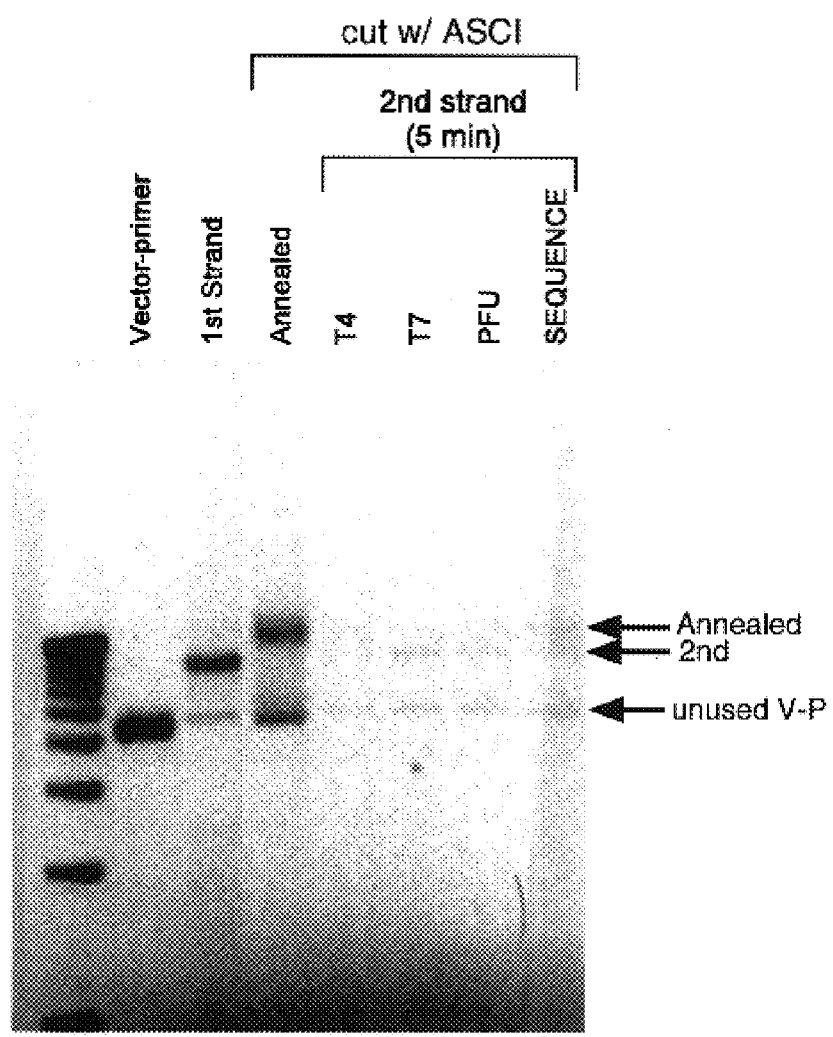

FIG. 16 is a digitized scan of cDNA molecules separated electrophoretically on an agarose gel, showing that T7 polymerase is the most effective in completion of second-strand synthesis as compared to T4, PFU (Promaga, Madison Wis.), and SEQUENASE (Amersham Pharmacia Biotech) DNA polymerases.

Figure 17:
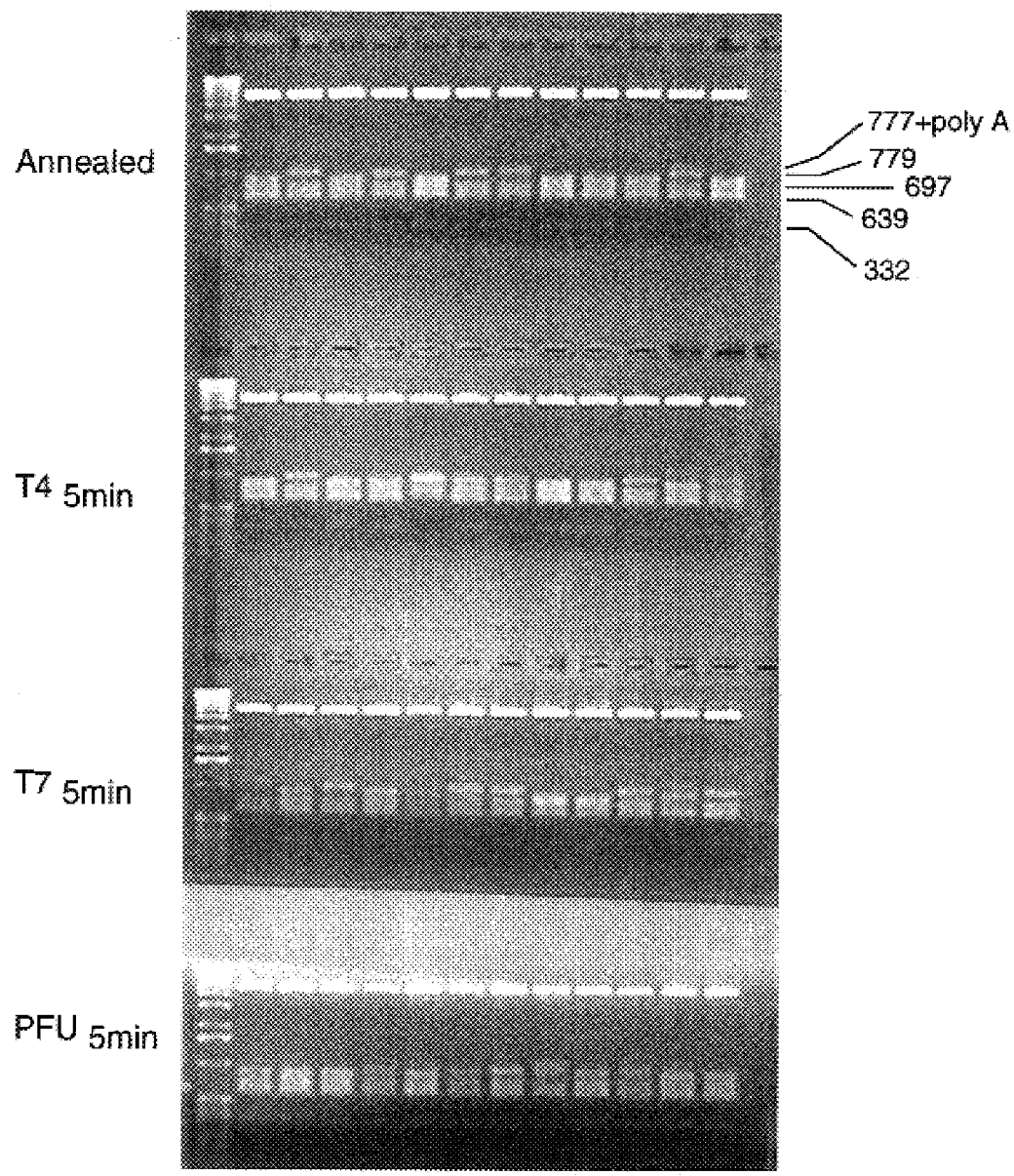

FIG. 17 is a digitized scan of cDNA molecules separated electrophoretically on a series of agarose gels, showing that the inclusion of tRNA in the RNAse digestion reaction prior to the second-strand synthesis reaction does not result in the inclusion of tRNA molecules in the cDNA reaction products. Further, this Figure shows that cDNA molecules produced without a second-strand synthesis ("Annealed" in the Figure) are capable of being transformed into host cells and are maintained therein.

DETAILED DESCRIPTION

The following examples, tables, and figures provide examples of ways in which the methods of the present invention may be accomplished. These examples are not intended to limit in any manner the number of ways in which these methods may be carried out by those of skill in the art, or the types of vectors, primers, and other materials that may be utilized in these methods. In particular, those of skill in the art will appreciate that by selecting different sequences for the 5' and 3' linkers (also interchangeably called primers throughout) of the present method, linkers (or primers) can be designed that will anneal to any vector of known nucleotide sequence digested with any particular restriction enzyme(s).

For example, the invention also includes polynucleotides with sequences complementary to those of the polynucleotides disclosed herein. The present invention also includes polynucleotides which are derived from the polynucleotides disclosed herein by any of the following or by a combination thereof: addition of residues; deletion of residues; substitution of residues, whether with polynucleotide residues or other molecules such as amino acids, carbohydrates, lipids, or modified forms thereof; or chemical modification of existing residues. Examples of chemical modifications include but are not limited to methylation, addition of other alkyl groups, addition of aromatic or heterocyclic molecules, addition or removal of a hydroxyl group, addition of polyethylene glycol, addition of carbohydrate, polypeptide, or lipid molecules, etc.

The present invention also includes polynucleotides that hybridize under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≥50 | 67° C.; 1xSSC -or- 45° C.; 1xSCC, 50% formamide | 67° C.; 0.3 x SSC |
| D | DNA:RNA | <50 | $T_D$*; 1xSSC | $T_D$*; 1xSCC |
| E | RNA:RNA | ≥50 | 70° C.; 1xSSC -or- 50° C.; 1xSSC, 50% formamide | 70° C. 0.3xSSC |
| F | RNA:RNA | <50 | $T_F$*; 1xSSC | $T_F$*; 1xSSC |
| G | DNA:DNA | ≥50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≥50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≥50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≥50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≥50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≥50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

‡: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†: SSPE (1xSSPE is 0.15 M NaCl, 10 mM $NaH_2PO_4$, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete.
*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$ (° C.) = (# of A + T bases) + 4(# of G + C bases). For hybrids between 18 and 49 base pairs in length, $T_m$ (° C.) = 81.5 + 16.6($\log_{10}[Na^+]$) + 0.41 (% G = C) − (600/N), where N is the number of bases in the hybrid, and [$Na^+$] is the concentration of sodium ions in the hybridization buffer ([$Na^+$] for 1xSSC = 0.165 M).

Additional examples of stringency conditions for polynucleotide hybridization are provided in Sambrook, J., E. F. Fritsch, and T. Maniatis, 1989, *Molecular Cloning: A Laboratory Manual,* Cold Spring Harbor Laboratory Press, Cold Spring Harbor, N.Y., chapters 9 and 11, and *Current Protocols in Molecular Biology,* 1995, F. M. Ausubel et al., eds., John Wiley & Sons, Inc., sections 2.10 and 6.3–6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

In particular, sequence identity may be determined using WU-BLAST (Washington University BLAST) version 2.0 software, which builds upon WU-BLAST version 1.4, which in turn is based on the public domain NCBI-BLAST version 1.4 (Altschul and Gish, 1996, Local alignment statistics, Doolittle ed., *Methods in Enzymology* 266: 460–480; Altschul et al., 1990, Basic local alignment search tool, *Journal of Molecular Biology* 215: 403–410; Gish and States, 1993, Identification of protein coding regions by database similarity search, *Nature Genetics* 3: 266–272; Karlin and Altschul, 1993, Applications and statistics for multiple high-scoring segments in molecular sequences, *Proc. Natl. Acad. Sci. USA* 90: 5873–5877; all of which are incorporated by reference herein). WU-BLAST version 2.0 executable programs for several UNIX platforms can be downloaded from the Washington University BLAST website. The complete suite of search programs (BLASTP, BLASTN, BLASTX, TBLASTN, and TBLASTX) is provided at that site, in addition to several support programs. WU-BLAST 2.0 is copyrighted and may not be sold or redistributed in any form or manner without the express written consent of the author; but the posted executables may otherwise be freely used for commercial, nonprofit, or academic purposes. In all search programs in the suite—BLASTP, BLASTN, BLASTX, TBLASTN and TBLASTX—the gapped alignment routines are integral to the database search itself, and thus yield much better sensitivity and selectivity while producing the more easily interpreted output. Gapping can optionally be turned off in all of these programs, if desired. The default penalty (Q) for a gap of length one is Q=9 for proteins and BLASTP, and Q=10 for BLASTN, but may be changed to any integer value including zero, one through eight, nine, ten, eleven, twelve through twenty, twenty-one through fifty, fifty-one through one hundred, etc. The default per-residue penalty for extending a gap (R) is R=2 for proteins and BLASTP, and R=10 for BLASTN, but may be changed to any integer value including zero, one, two, three, four, five, six, seven, eight, nine, ten, eleven, twelve through twenty, twenty-one through fifty, fifty-one through one hundred, etc. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

A number of types of cells may act as suitable host cells to be transformed with the products of the cDNA library preparation reactions. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Alternatively, it may be possible to use host cells such as lower eukaryotes like yeast or prokaryotes such as bacteria. Potentially suitable yeast strains include *Saccharomyces cerevisiae, Schizosaccharomyces pombe,* Kluyveromyces strains, Candida, or any yeast strain capable of being transformed with cDNA clones. Potentially suitable bacterial strains include *Escherichia coli, Bacillus subtilis, Salmonella typhimurium,* or any bacterial strain capable of being transformed with cDNA clones.

Patent and literature references cited herein are incorporated by reference as if fully set forth.

In this proposal, we describe a strategy (compared to Kato et al., 1994) that we call Primers-Attached-Vector-Elongation (PAVE). The crucial element of the strategy is a novel vector attached with primers for both first strand and second strand cDNA synthesis. The oligo-dT primer attached to one end of the vector is used to prime first-strand cDNA synthesis from the poly(A) stretch of the mRNA, whose cap has been specifically labeled with a 27-mer biotinylated RNA tag. After digestion of the single-stranded RNA with RNase 1, full-length cDNA is captured by streptavidin beads. Second strand synthesis is then carried out using the primer (with sequence identical to the RNA tag) at the other end of the vector, which would specifically base pair with a full-length cDNA that contains a sequence complementary to the RNA tag. This will give rise to a circularized plasmid for subsequent *E. coli* transformation. Since no DNA ligation will be necessary after cDNA synthesis, all the possible artifacts generated by cDNA-vector ligation will be theoretically eliminated. In addition, the availability of double-strand vectors containing single-strand cDNA inserts before the second strand cDNA synthesis provides a mechanism for library normalization and substraction and would also allow subgrouping the cDNA libraries into the subset encoding secreted and membrane proteins and the subset encoding soluble proteins.

EXAMPLES

Example 1

Preparation of Vector-primer

Plasmid vector pED6dpc4 was completely digested with EcoR I and Sal I. Thirty micrograms of digested plasmid DNA was then ligated with 840 pmol each of the following two linkers:

```
Linker 1
Phosphate-5'-
AATTCGAGTGAACACTCGAGCTCACTAGTGACCAGCTGATGCGCCTCAAA-3'          (SEQ ID NO:1)
```

```
                        -continued
3'-GCTCACTTGTGAGCTCGAG-5'                           (SEQ ID NO:2)

Linker 2
5'-CTAATCTGATCCGCTAGTGGTAC-3'                       (SEQ ID NO:3)

3'-(T)30GATTAGACTAGGCGATCACCATGAGCT-5'-Phosphate    (SEQ ID NO:4)
``` in a 1.4 ml reaction volume using T4 DNA ligase (NEB) under conditions suggested by the manufacturer. The ligated plasmid DNA was then purified through electrophoresis on a 0.8% agarose gel.

Example 2

Ligation of a Biotinylated RNA Tag to the 5'-end of Full-length mRNA

Ten ug of rabbit globin mRNA was treated with 5 units of HK phosphatase (Epicentre) in a total volume of 250 ul under conditions recommended by the manufacturer. After incubation at 37° C. for 30 min, the mixture was extracted with phenol/chloroform and precipitated with NaOAc/ethanol. The pellet was dissolved in 20 ul of DEPC-treated water and 19.5 ul of which was subjected to digestion with 5 units of tobacco acid pyrophosphatase (TAP) in a 50 ul volume. The reaction was carried out at 37° C. for 30 min and terminated by phenol/chloroform extraction. After NaOAc/ethanol precipitation, the pellet was dissolved in 20 ul of DEPC-treated water. Fifteen ug of TAP treated RNA was then ligated to 7 ug of RNA tag (27-mer synthetic ribonucleotide with 5' biotin group) in a 120 ul reaction mixture containing 50 mM Tris-Cl, pH 7.8, 10 mM MgCl2, 10 mM DTT, 1 mM ATP and 12 units of T4 RNA ligase (Takara). After overnight incubation at room temperature, the sample was extracted twice with phenol/chloroform and precipitated with NaOAc/ethanol. The pellet was dissolved in DEPC-treated water.

As a control experiment, 2.5 ug of the TAP treated RNA was ligated to 2.5 ug of 5' biotinylated DNA tag in a reaction volume of 40 ul and the sample was treated as described above.

Figure 1:
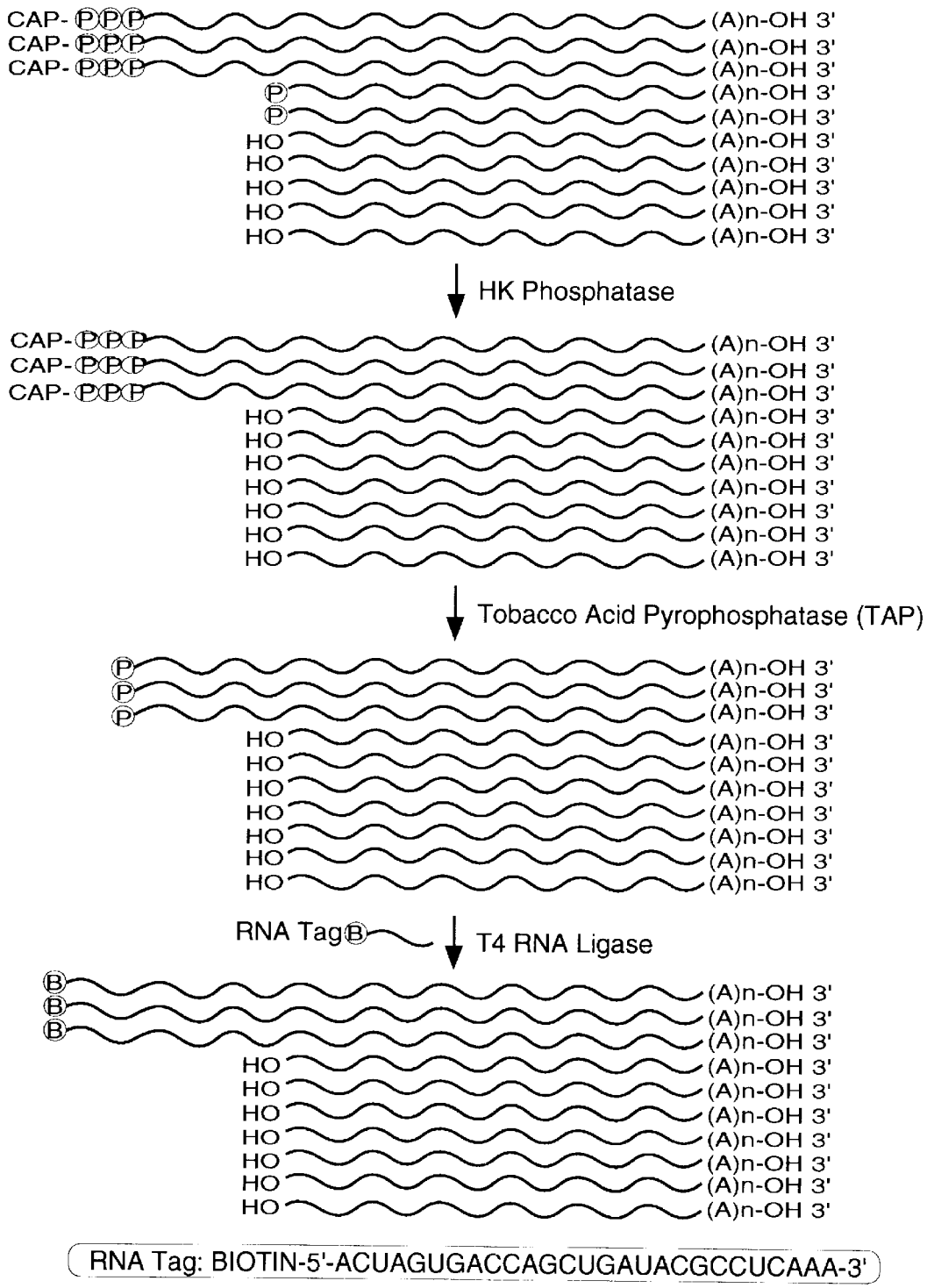
FIG. 1 is a schematic representation of the disclosed method for preparing mRNA molecules for cDNA library construction: mRNA is treated with phosphatase and then with pyrophosphatase, followed by ligation with RNA ligase to add an RNA tag (SEQ ID NO: 8) to the 5' phosphate that will only be present on full-length mRNA molecules.
Figure 2:
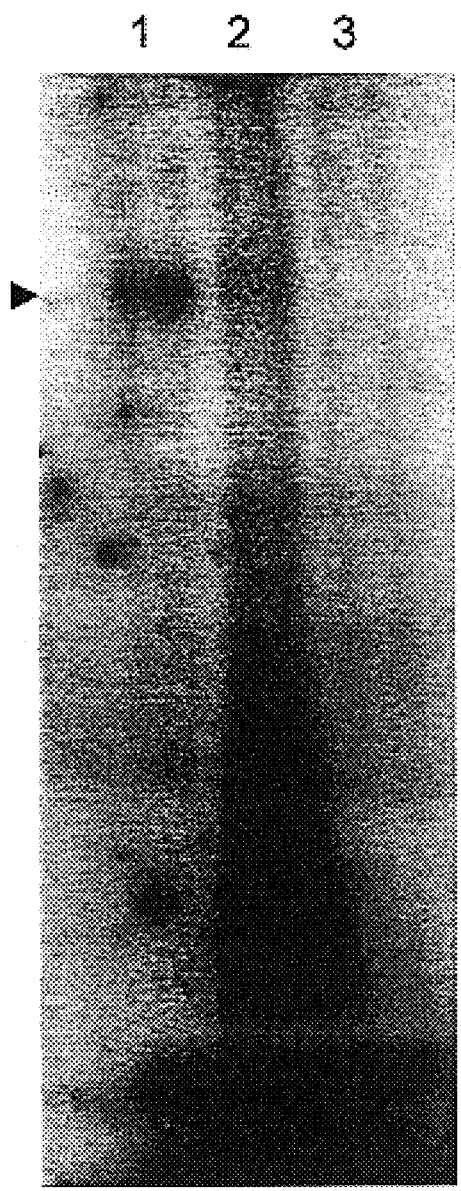
FIG. 2 is an autoradiograph of a Northern blot showing the ligation of tobacco acid pyrophosphatase (TAP)-treated (lanes 1 and 2) or capped (no TAP treatment, lane 3) rabbit globin mRNA with either an RNA tag (lanes 1 and 3) or a DNA tag (lane 2) using T4 RNA ligase. The blot was hybridized with a radioactively labeled oligodeoxy-nucleotide complementary to the tag sequence. The arrow points to the position of full-length tagged rabbit globin mRNA. This Northern blot indicates that TAP treatment is necessary for efficient RNA ligation, and that, as compared to DNA tags, RNA tags are more efficiently ligated to mRNA molecules by T4 RNA ligase.
Figure 3:
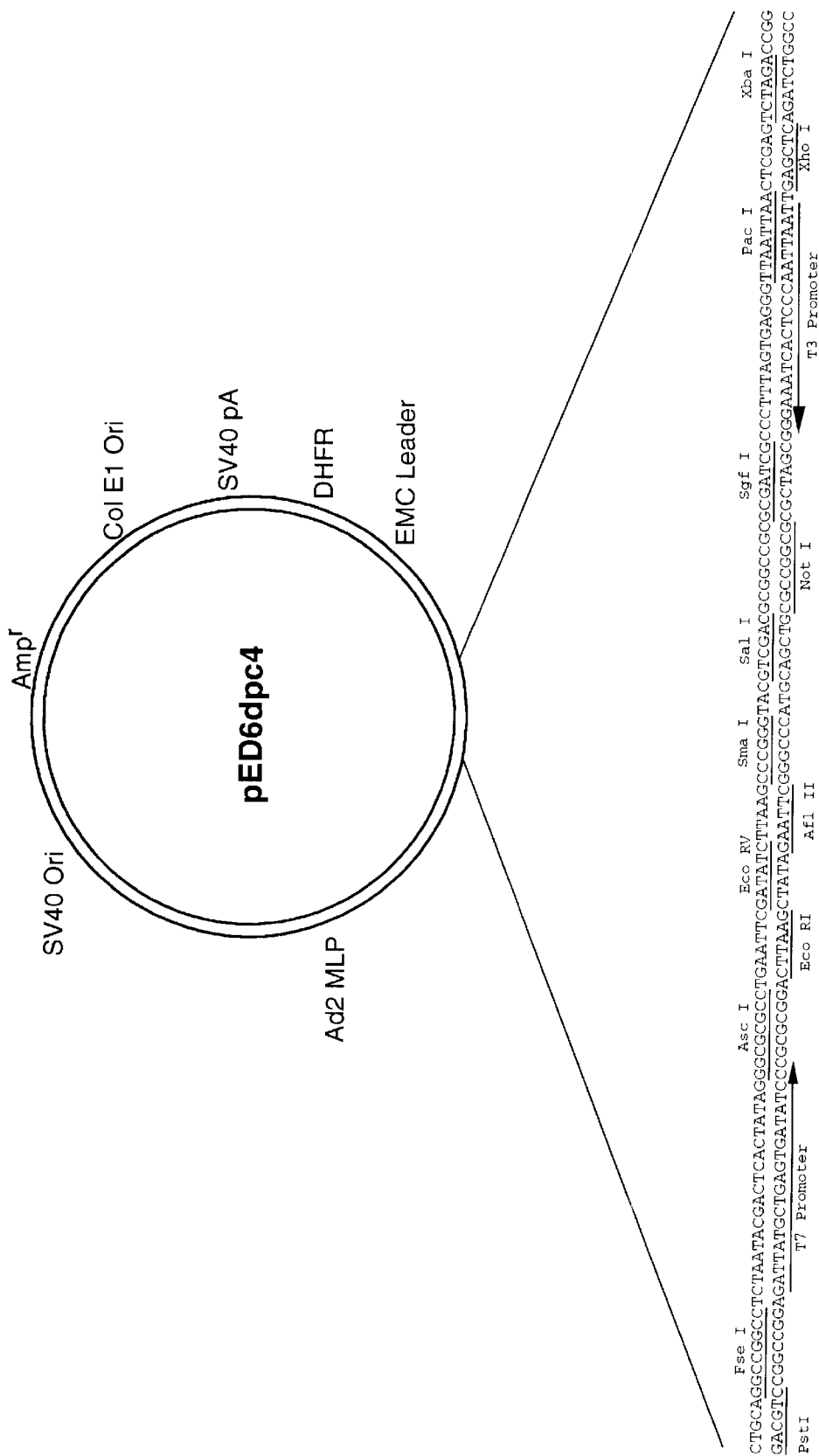
FIG. 3 is a schematic representation of the pED6pdc4 vector that may be used for construction of cDNA libraries as disclosed herein, and includes the nucleotide sequence (SEQ ID NO: 9) of the polylinker region of the pED6pdc4 vector.
Figure 4:
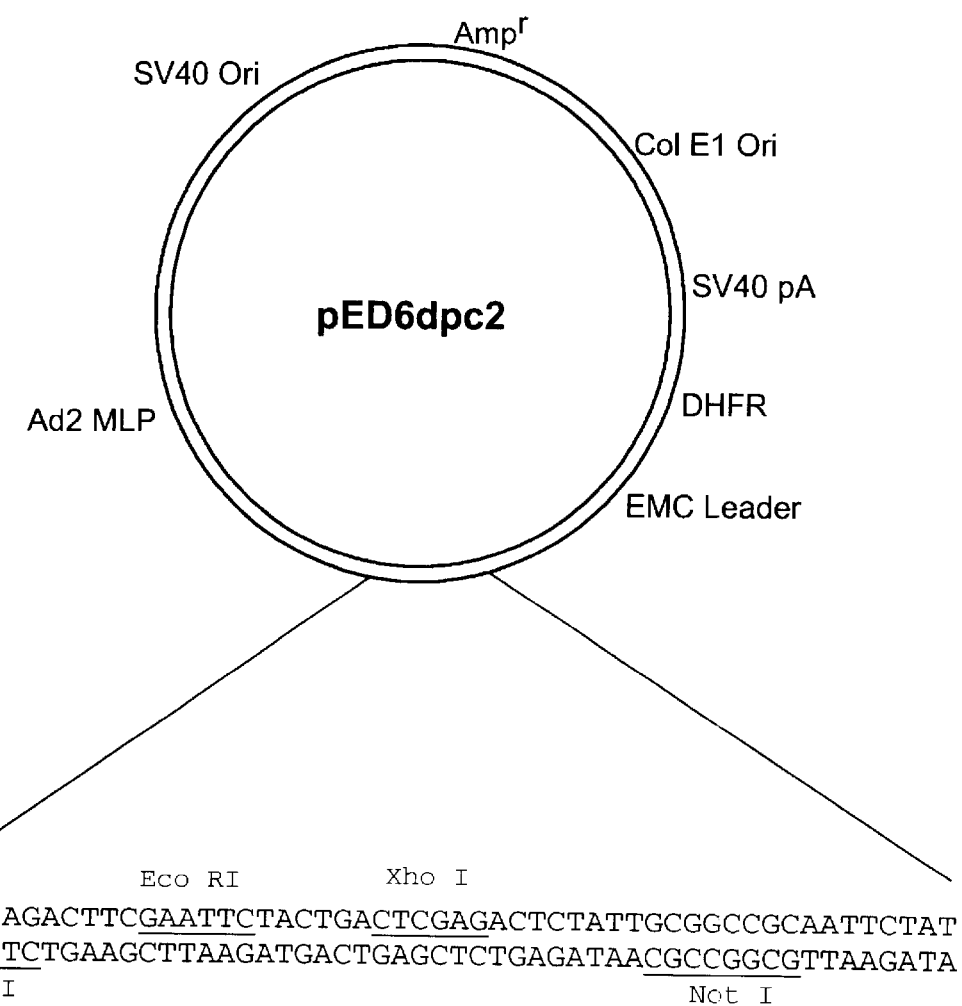
FIG. 4 is a schematic representation of the pED6pdc2 vector from which the pED6pdc4 vector was derived, and includes the nucleotide sequence (SEQ ID NO: 10) of the polylinker region of the pED6pdc2 vector.
Figure 5:
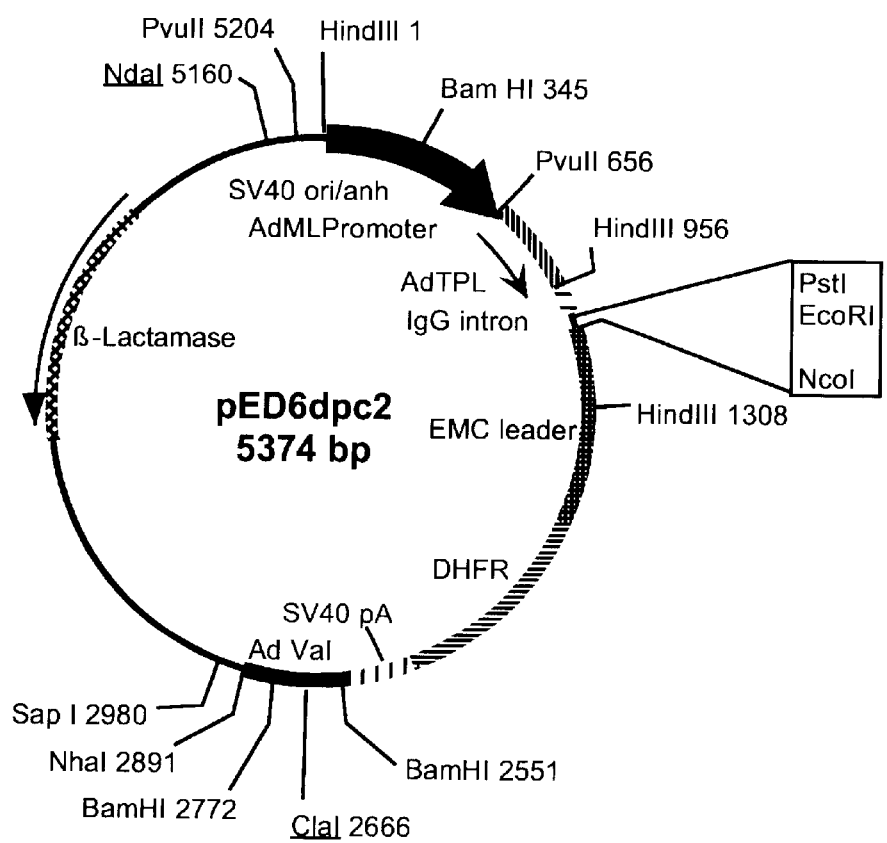
FIG. 5 is another schematic representation of the pED6pdc2 vector and contains more information concerning the attributes of the pED6pdc2 vector. The pED6dpc2 vector was derived from pED6dpc1 by insertion of a new polylinker to facilitate cDNA cloning (Kaufman et al., 1991, Nucleic Acids Res. 19: 4485–4490).

To assess the efficiency for ligating the RNA or DNA tag to rabbit globin mRNA, 0.25 ug of the RNA samples were electrophoresized on a 4–20% TBE/PAGE minigel (Novex) and blotted onto nylon-plus membrane (QIAGEN). After hybridization with 32P-labeled anti-tag (SEQ. ID. No. #5'-GAGGCGTATCAGCTGGTCACT-3') according to Sambrook et al., 1989, the position of mRNA molecules ligated with either the RNA or DNA tag was revealed by autoradiography. As judged from FIG. 4, RNA tag is ligated to the TAP-treated mRNA much more efficiently than the DNA tag.

Example 3 cDNA Synthesis and Cloning

Approximately 1.25 ug of biotin-RNA-tagged mRNA was mixed with 1.2 ug of vector-primer in a final volume of 20 ul containing 50 mM Tris-Cl, pH 8.3, 75 mM KCl, 3 mM MgCl2, 10 mMDTT, 0.5 mM each of the four dNTPs and 200 units of Superscript II (GIBCO BRL) and the reaction was carried out at 48° C. for 1 hour. The cDNA was then extracted with phenol/chloroform and precipitated with ethanol. The pellet was dissolved in water and digested with 25 units of Rnase One (Promega) and 6 units of *E. Coli* RNase H (Epicentre) in 60 ul of reaction mixture containing 10 mM Tris-Cl, pH 7.9, 10 mM MgCl2, 50 mM NaCl and 1 mM DTT. After 1 hour incubation at 37° C., 30 ul of water and 10 ul of 10×annealing buffer (0.5 M Tris-Cl, pH 8.0, 0.1 M MgCl2 and 0.5 M NaCl) were added and the mixture was heated at 70° C. for 5 min and slowly cooled down to 50° C. in 30 min. Ten ug of glycogen was then added the DNA was precipitated in NaOAc/ethanol.

For second-strand cDNA synthesis, the above DNA pellet was dissolved in 13 ul of water and 2 ul of 10×T4 DNA polymerase buffer (NEB), 4 ul of dNTPs (2.5 mM each), 1 ul of 1 mg/ml of BSA and 1 ul (3 units) of T4 DNA polymerase were subsequently added. After 1 hour at 37° C., the DNA was precipitated and used to transform competent *E. coli* cells (DH10B, GIBCO BRL).

When tagged rabbit globin mRNA was used in the above procedure, the efficiency of the library is about $10^6$ colonies/ug of starting mRNA.

When plasmids were isolated from randomly picked individual colonies and digested with Asc I and Not I to release the insert, 37 out of 48 colonies have full-length (about 650 bp) cDNA inserts. In addition, 5'-end and 3'-end DNA probes were used to hybridize to duplicate filters lifted from plated colonies and 75.8% of the colonies are full-length as judged by being able to hybridize to both probes (Table 1).

Experimental Design and Expected Results

I. Construction of a Multi-purpose Vector (pAVE1) for in vitro and in vivo Protein Expression A vector PAVE1 has been constructed for our large scale molecular biology effort to obtain the full-length cDNAs of all the human secreted proteins in a single cloning step. pAVE1 is derived from pNOTS by replacing its Pst I/Xho I fragment with a 100 bp designed linker. Some of the notable features of pAVE1 include:

- A). T7 and T3 RNA polymerase promoters flanking the cDNA insert to be cloned from 5' to 3' into the Eco RI and Kpn I sites, allowing sense and anti-sense RNA molecules to be synthesized, respectively. The T7 RNA promoter also allows coupled in vitro transcription and translation (TNT) protocol to be used to assess the size of the encoded protein products.
- B). Four eight-base recognizing restriction sites flanking T7 and T3 promoters, permitting easy subcloning of the cDNA inserts.
- C). Suitable for COS expression because of the SV40 origin and the eukaryotic expression cassette.
- D). The f1 origin (from the pNOTS backbone) would allow ssDNA to be prepared for library subtraction and normalization. In addition, recombinant f1 phage particles can be used to transfect COS cells (Yokoyama-Kobayashi and Kato, 1993). If we could engineer a patentable COS cell line that can specifically and efficiently endocytosize f1 phage particles, then we can carry out COS transfection in a large scale fashion without the need for plasmid preparation.

II. Preparation of Primers-attached-vector

Eco RI and Kpn I digested pAVE1 plasmid DNA will be gel-purified and ligated to the 5'-end linker, which is compatible with the Eco RI end and contains a single-stranded sequence identical to the RNA tag, and to the 3'-end linker, which is compatible with the Kpn I end and contains single-strand oligo-dT sequence. The ligated DNA product will be gel-purified and the presence of the primers will be confirmed by digestion with Hind III and Bst XI followed by polyacrylamide gel analysis. More than 90% of the vector should be attached with the two primers if the proper linker/vector ratio is used. Otherwise, the desired primers-attached vector DNA should be purified by consecutive oligo-dA column and anti-RNA tag oligonucleotide column.

III. Tagging the Cap of the mRNA with Oligoribonucleotides

The mRNA samples will be treated with the heat-killable (HK) phosphatase isolated from an antarctic bacterium (Epicenter) to remove the phosphate group at the 5'-ends of degraded RNA molecules. The cap of the full-length RNA population will be removed with tobacco acid pyrophosphatase (TAP; Shinshi et al., 1976a and 1976b; Efstratiadis etal., 1977; Fromont-Racine, et al., 1993; Maruyama and Sugano, 1994; Kato et al., 1994). The decapped mRNA molecules will then be ligated to a 27-mer biotinylated oligoribonucleotide (RNATAG, using T4 RNA ligase. The small RNA tag was the removed by repetitive ethanol precipitation.

There are two limitations for this procedure, i.e., the low ligation efficiency (about 60%, Tessier, et al., 1986) and the small proportion of mRNA-mRNA ligation. However, since selection of full-length cDNA will be applied after first strand cDNA synthesis (RNase I digestion followed by streptavidin capture) and during second strand synthesis (specific priming from the vector-attached primer), this may not have a great detrimental effect on the quality of the cDNA library (although it can reduce the number of colonies produced from a definite amount of mRNA).

IV. First Strand cDNA Synthesis and Full-length cDNA Enrichment

The tagged mRNA will be annealed to the primers-attached-pAVE1 vector and first strand cDNA synthesis will be carried out using Superscript II reverse transcriptase (GIBCO-BRL). The first strand cDNA, together with the associated mRNA template, will be precipitated and subject to RNase I digestion to degrade unprotected single-strand RNA regions as well as unreacted free mRNA molecules.

In this reaction, only the biotin group of the mRNA whose cDNA is full-length will be protected from clipping off the vector-primer-cDNA assembly. The full-length cDNA-vector molecules will then be captured using streptavidin magnetic beads and subject to complete RNase H and alkaline hydrolysis to remove the RNA strand. This will produce a population of single-strand full-length cDNA covalently linked to the pAVE1 vector through the poly (A/T) region. The full-length cDNA population will account for about 7–10% of the total cDNA synthesized by reverse transcriptase according to Carninci et al., 1996.

V. Second Strand cDNA Synthesis and Transformation

The cDNA-vector molecules will be diluted, denatured and reannealed to allow base pairing between the vector-attached primer and the extreme 3' end of the single-strand full-length CDNA. Second strand CDNA will be synthesized using T4 DNA polymerase. The resulting double-stranded circular DNA (with two gaps at each end of the cDNA) will be used to transform *E. coli* strain 10B or DH5α. More than $10^6$ primary colonies should be obtained for each microgram of vector-primer.

VI. Assessment of the Quality of the cDNA Library

A). Globin mRNA control

Pure globin mRNA (about 700 bases for both subunits) will be used to prepare a PAVE cDNA library. Duplicate filters from plates containing a total number of at least 10,000 colonies will be hybridized with the 5'-end probe and the 3'-end probe, respectively. The ratio of 5'-end positive clones to the 3'-positive clones should be close to 1. At least 100 primary colonies will be picked for plasmid DNA preparation. Insert size will be determined by Asc I/Not I digestion. At least 90% of the colonies should have a full-length cDNA insert.

B). A real cDNA library

A PAVE cDNA library will be made from some mRNA isolated from a human tissue source, preferably pancreas. The GAPDH 5'- and 3'-end probes will be used for colony hybridization to assess the ratio of clones containing GAPDH cDNA inserts with 5' and 3'sequences. If the ratio is close to 1 as expected, 300 colonies will be randomly picked from the entire library for plasmid preparation and the insert size will be determined for each clone. More than 95% of the clones should have a cDNA insert. In addition, the plasmid DNA sample will be subject to coupled in vitro transcription and translation (TNT) analysis in the presence of $^{35}$S-labeled methionine. The size of the synthesized protein will be analyzed by 4–20% SDS-PAGE followed by autoradiography. If more than 90% of the insert-containing clones give rise to a protein product in the TNT assay, 3000 colonies will be subjected to 5'-end sequencing and the data will be subjected to bioinformatics evaluation.

An additional, and perhaps more rigorous, approach to evaluate quality of the library is to screen for the presence of the 7 kb full-length cDNA for human cPLA2β, whose mRNA is ubiquitously expressed but most abundant in pancreas. Previous effort has produced more than 100 positive clones from four cDNA libraries and none of them is full-length (Song, Kriz, Bean and Knopf, Unpublished).

Future Considerations

The following efforts should be considered to expedite our progress in cloning all the human cDNAs for secreted or membrane proteins and to facilitate their functional analysis:

I. Enrichment of cDNAs for Secreted and Membrane Proteins

Strategy 1: Highly pure rough ER will be isolated by refining the sucrose-density centrifugation parameters. The mRNA molecules will be isolated, their poly A tails removed by oligo (dT)-directed RNase H digestion and the 5'-end cap labeled by biotin (Carninci, et al., 1996). The labeled rough ER mRNA will be hybridized with the single-stranded cDNA-vector population prepared from high quality total mRNA. After capture with streptavidin beads, the bound cDNA will be eluted and used to prepare a subset of cDNA library which should be highly enriched in cDNA molecules for secreted or membrane-bound proteins.

Strategy 2: Explore the possibility of in vitro TNT based library subgrouping: Plasmid DNA from a PAVE cDNA library will be prepared and subject to in vitro TNT for a defined length of time. Inhibitors for T7 RNA polymerase and the translation machinery will be added to freeze the cDNA-RNA-nascent peptide complex. If the nascent peptide contains a secretion signal, the complex will be captured by a solid phase conjugated with signal recognition particle (SRP). The captured cDNA-vector population will be used to transform *E. coli* cells to create a subset enriched in cDNAs for proteins with a signal peptide.

II. Subtraction

The full-length cDNA clones for the most abundant mRNA species will be obtained when we sequence our first 3000 clones for library quality assessment. These clones will be collected and biotinylated sense RNA transcripts will be made from the Not I linearized plasmid DNA using T7 polymerase. After removal of the 5' and 3' vector sequences on the RNA using an oligonucleotide-directed RNase H digestion approach, the remaining RNA will be used to subtract their corresponding cDNAs from the single-strand cDNA-vector population. The remaining cDNA-vector population should be enriched with rare messages.

III. Normalization

Normalization of PAVE libraries could be carried out before the initial bacteria transformation step, unlike in the original normalization protocol where amplified single-strand phagmid DNA was used (Soares, et al., 1994). Therefore, normalized PAVE cDNA libraries should have the same cDNA representation as the unnormalized primary library, minimizing the chance of losing some cDNAs that are selected against during amplification.

IV. An ES Cell Line Library?

If we succeed in constructing normalized PAVE cDNA library with more than 95% of the inserts being full-length and encoding a protein product by TNT assay, then we can design a special vector which can direct the recombination of the cDNA insert into a specific locus in the mouse genome. Linearized plasmid DNA prepared from the library will be used to transfect ES cells. The ES cells containing individual cDNA inserts at the expected location will be isolated and the identity of the cDNA analyzed by PCR and sequencing. Eventually, we should be able to establish an ES cell line library for convenient transgenic mice production. This is opposite to the Merck-Lexicon approach, where ES cell lines with disrupted genes are collected for production of knock-out mice, but maybe more relevant to the drug-discovery scenario, since most drugs are inhibitors to a disease target.

Tagging of mRNA

Do all RNA set-up in tissue culture hood

Do the following in silconized RNASE-FREE 1.5 ml tubes (Ambion).

ALL reagents are made in DEPC-WATER (Ambion).

Use only ART tips for all reactions.

Clean pipettes with RNASE AWAY and EtOH.

Place a new piece of lab paper on your bench (plastic side up).

Wear gloves at all times!!!!

IN GENERAL, CLEAN UP YOUR WORK AREA!!!!!! (RNASES are EVERYWHERE.)

Day One

Today: We are using 0.24–9.5 KB markers (1 μg/μl), TF-1 mRNA (1 μg/μl) & Globin mRNA (1 μg/μl)

| 1 μl | tRNA (5 μg/μl) | (Ambion) |
|---|---|---|
| 36 μl/39 μl | DEPC-Water | (Gibco) |
| 5 μl | 10X BAP Buffer | (Homemade-Sigma) |
| 0.75 μl | 0.1 M DTT | (Promega) |
| 1.25 μl | RNAsin (40 u/μl) | (2 μg) |
| 5 μl | mRNA (1 μg/μl) | (Gibco) |
| 1 μl | BAP (150 u/μl) | |
| $V_T$ =50 μl | | |

Incubate at 37° C. for 0.5 hours on a heating block with cover (pipette box top). If there is condensation, then do a quick spin.

Add 100 μl of DEPC-water then add 150 μl of phenol/CHCl3/IAA pH 7.9 (Ambion) and "flick" for 0.5 min. Spin 4–6 minute in microcentrifuge at 14,000 rpm. Remove 125 μl aqueous layer with pipette (TOP) and place into new 1.5 ml RNASE-FREE tube.

Add 125 μl of DEPC-water (Ambion) to the original tube (bottom) and "flick" for 30 seconds. Spin for 4–6 minutes in microcentrifuge at 14,000 rpm. Remove 125 μl aqueous layer with pipette (TOP) and place with the other aqueous layer in the 1.5 ml RNASE-FREE tube.

Add 25 μl 3M NaOac, pH 4.5 (Autoclaved from media prep) and 625 μl of 100% EtOH. Incubate on dry ice for 5–8 minutes.

Spin for 10–15 minutes at 4° C. at 14,000 rpm. Remove and SAVE (in a 1.5 ml RNASE-FREE tube) all of the EtOH layer except approximately 50 μl. Spin as above for 5 minutes. Remove the remaining EtOH without disrupting the pellet. Wash pellet with 200 μl of 80% EtOH chilled at −20° C. and spin for 2–5 minutes at 4° C. at 14,000 rpm. Remove EtOH and again spin for 1 minute at 14,000 RPM and remove the remaining 1–5 μl of EtOH by just touching a 20 μl pipette tip to the edge of the drop of EtOH. Air dry with lids open on ice for 5 minutes.

Resuspend in 20 μl DEPC-Water (Ambion) (100 ng/μl).

Save 500 ng (5 μl) of RNA markers only.

| 1 μl | tRNA (5μg/μl) | (Ambion) |
|---|---|---|
| 21.7 μl/26.7 μl | DEPC-water | (Epicenter) |
| 5 μl | 10X TAP buffer | (Promega) |
| 1.3 μl | RNAsin | (Epicenter) |
| 20 μl/15 μl | "BAP-ed" mRNA | |
| 1 μl | TAP (10 u/μl) | |
| Vt = 50 μl | | |

Incubate at 37° C. for 0.5 hour on a heating block with cover (pipette box top). If there is condensation, then do a quick spin.

Add 150 μl water. Add 150 μl of phenol/CHCl3/IAA pH 7.9 (Ambion) and "flick" for 30 seconds. Spin for 4–6 minutes in microcentrifuge at 14,000 rpm. Remove 125 μl aqueous layer with pipette (TOP) and place into new 1.5 ml RNASE-FREE tube.

Add 125 μl of DEPC-water (Ambion) to the original tube (bottom) and "flick" for 30 seconds. Spin for 4–6 minutes in microcentrifuge at 14,000 rpm. Remove 125 μl aqueous layer with pipette (TOP) and place with the other aqueous layer in the 1.5 ml RNASE-FREE tube.

Add 25 μl 3M NaOAc, pH 4.5 (Autoclaved from media prep) and 625 μl of 100% EtOH. Incubate on dry ice for 5–8 minutes.

Spin for 10–15 minutes at 4° C. at 14,000 rpm. Remove and SAVE (in a 1.5 ml RNASE-FREE Tube) all of the EtOH layer except approximately 50 μl. Spin as above for 5 minutes. Remove the remaining EtOH without disrupting the pellet. Wash pellet with 400 μl of 80% EtOH chilled and spin for 2–5 minutes at 4° C. at 14,000 rpm. Remove EtOH and again spin for 1 minute at 14,000 RPM and remove the remaining 1–5 μl of EtOH by just touching a 20 μl pipette tip to the edge of the drop of EtOH. Air dry with lids open on ice for 5 minutes.

Resuspend in 20 μl DEPC-Water (Ambion) (75 ng/μl)

Save 500 ng (6.7 μl) of RNA markers only

Ligase Buffer: 0.25 M Tris pH7, 0.25 M Tris pH8, 0.1M, MgCl2 (ALL Ambion Solutions)

You have approximately 2 μg to ligate at this point.

(1) RNA Markers, (2) Globin, (3) TF-1 mRNA

| | | |
|---|---|---|
| 1 µl | tRNA (5 µg/µl) | (Ambion) |
| 56.95 µl/58 µl/64.7 µl | DEPC-Water | (HOMEMADE-see recipe) |
| 10 µl | 10X New Ligase Buffer | (HOMEMADE-see recipe) |
| 1 µl | IM DTT | (Promega) |
| 2.5 µl | RNAsin (40 u/µl) | (Gibco-BRL) |
| 1.8 µl | FRESH 10 mM ATP | (IDT) |
| 1.75 µl/0.7 µl/0.7 µl | RNA-TAG (100 pmol/µl) | (ABOVE reaction) |
| 20µ/20 µl/13.3 µl | TAP-treated mRNA (2 µg) | (GIBCO-BRL) |
| 5 µl | T4 RNA Ligase (5 u/µl) | |
| $V_T$ = 100µ | | |

Incubate at 16° C. for 16 Hours (Overnight).
Add 50 µl of DEPC-water. Add 150µ of phenol/CHCl$_3$/IAA pH 7.9 (Ambion) and "flick" for 30 seconds. Spin for 4–6 minutes in microcentrifuge at 14,000 rpm. Remove 125 µl aqueous layer with pipette (TOP) and place into now 1.5 ml RNASE-FREE tube.

Add 125 µl of DEPC-water (Ambion) to the original tube (bottom) and "flick" for 30 seconds. Spin for 4–6 minute in microcentrifuge at 14,000 rpm. Remove 125 µl aqueous layer with pipette (TOP) and place with the other aqueous layer in the 1.5 ml RNASE-FREE tube.

Add 25 µl 3M NaOAc, pH 4.5 (Autoclaved from media prep) and 625 µl of 100% EtOH. Incubate on dry ice for 5–8 minutes.

Spin for 10–15 minutes at 4° C. at 14,000 rpm. Remove and SAVE (in a 1.5 ml RNASE-FREE tube) all of the EtOH layer except approximately 50 µl. Spin as above for 5 minutes. Remove the remaining EtOH without disrupting the pellet. Wash pellet with 400 µl of 80% EtOH chilled and spin for 2–5 minutes at 4° C. at 14,000 rpm. Remove EtOH and again spin for 1 minute at 14,000 RPM and remove the remaining 1–5 µl of EtOH by just touching a 20 µl pipette tip to the edge of the drop of EtOH. Air dry with lids open on ice for 5 minutes.

Resuspend in 4 µl DEPC-Water (Ambion) (250 ng/µl) (markers), (500 ng/µl) (mRNA)
Save 500 ng (2 µl) of RNA markers
Day Two
Continue with 2µg and 5µl of TF-1 mRNA (for biotin-capture).
1$^{st}$ Strand Synthesis
Add components in the order they are listed.

| | | |
|---|---|---|
| 1.0 µl | 1.0 µl | tRNA |
| | 1.0 µl | DEPC-treated water |
| | 4.0 µl | 5X 1st Strand Buffer |
| | 2.0 µl | 100 mM DDT |
| | 0.5 µl | 20 mM dNTPs (fresh) |
| 4.7 µl | 3.7 µl | pED4 NT35 (Jul. 14,1998, 300 ng/µl) total 1.1 µg |
| | 0.5 µl | RNAsin |
| | 4.0 µl | Globin mRNA (total 1 µg)/MG63 mRNA (total 2 µg) |
| | 2.0 µl | Superscript II (Gibco-BRL) |
| | 1.3 µl | Thermoscript RT |
| $V_T$ = 20 µl | | |

Incubate at 48° C. for 1 hour, 55° for 30 minutes
Add 130 µl of water and 150 µl of phenol/CHCl$_3$/IAA pH 7.9 (Ambion) and "flick" for 0.5 min. Spin for 4–6 minute in microcentrifuge at 14,000 rpm. Remove 125 µl aqueous layer with pipette (TOP) and place into new 1.5 ml RNASE-FREE tube.

Add 125 µl of DEPC-water (Ambion) to the original tube (bottom) and "flick" for 30 seconds. Spin for 4–6 minutes in microcentrifuge at 14,000 rpm. Remove 125 µl aqueous layer with pipette (TOP) and place with the other aqueous layer in the 1.5 ml RNASE-FREE tube.

Add 25 µl 3M NaOac, pH 4.5 (Autoclaved from media prep) and 625 µl of 100% EtOH. Incubate on dry ice for 5–8 minutes.

Spin for 10–15 minutes at 4° C. at 14,000 rpm. Remove and SAVE (in a 1.5 ml RNASE-FREE tube) all of the EtOH layer except approximately 50 µl. Spin as above for 5 minutes. Remove the remaining EtOH without disrupting the pellet. Wash pellet with 400 µl of 80% EtOH chilled at −20° C. and spin for 2–5 minutes at 4° C. at 14,000 rpm. Remove EtOH and agin spin for 1 minute at 14,000 RPM and remove the remaining 1–5 µl of EtOH by just touching a 20 µl pipette tip to the edge of the drop of EtOH. Air dry with lids open on ice for 5 minutes.

Resuspend in 51.5 µl of DEPC-treated water.
0.8% TBE Agarose Gel
Use only depyrogenated glassware to make the buffer and the gel.
Wash your gel box and casting tray with RNASE AWAY.
Make 1×TBE Buffer, by adding 110 ml of 10×TBE to 1L of sterile milli-Q water. You may need to make 2 bottles, depending on the size of your gel.

Using a depyrogenated graduated cylinder measure 120 ml of 1×TBE buffer and pour it into a 500 ml depyrogenated flask. Measure out 1 g of ultra-pure agarose (BI 101) by shaking it into a weigh boat. Add the agarose to the buffer in the flask and swirl.

Heat the agarose approximately 1.5 minutes in a microwave, or until the agarose is clear. Allow it to cool until you can touch it with your bare hands without it burning, approximately 10 minutes. Add 10 µl of 10 mg/ml ethidium bromide, swirl and pour it into a casting tray. Add comb to the gel and remove all bubble with a pipette tip.

Wait until it is completely solidified, approximately 20 minutes. In the meantime, add Gel Loading Buffer II (Ambion) in equal volume with your saved samples from the previous three reactions. (Example: if you saved 1 µl then you add 1 µl of dye.) You should have 3 samples of RNA markers at after various reactions. Also, add 0.5 µl of 0.24–9.5 KB RNA Ladder (Gibco-BRL) with 2 µl of water and 2 µl of dye for your gel marker.

Heat 200 ml of sterile milli-Q water in a 500 ml beaker in the microwave until it boils or set up a 80° C. heat block. Place your gel sample with dye into the water for 5 minutes at 80° C. Then place them directly on to ice, until you are ready to load them onto the gel.

Once the gel is hardened place it into the buffer chamber and add buffer to cover it. Load your sample onto the gel. Run the gel at 100 volts for approximately 1 hour, or until the first dye line reaches 2/3ths of the length of the gel. Stop the gel and take a picture.

You may have lost some mRNA as you progressed through each reaction, show by the decrease in intensity of the stained mRNA; HOWEVER, the mRNA should all be the same size on the gel. If degradation has occurred, there will be a downshift in the size of the mRNA as the process progressed.
RNASE-treatment

| | | |
|---|---|---|
| 52.0 µl | 51.5 µl | cDNA (1.1 µg) |
| | 6.0 µl | 10X NEB buffer #2 |
| | 2.0 µl | Rnase One (Promega, 10 U/µl) |
| | 0.5 µl | E. coli RNAse H (Epicenter) (10 u/µl) |
| $V_T$ = 60 µl | | |

Incubate at 37° C. for 60 minutes

Stop the 5 µg cDNA library

Annealing

JCB Annealing Buffer=30 mM Tris pH 8, 10 mM MgCl$_2$, 300 mM NaCl (made with Ambion Solutions)

| | |
|---|---|
| 60 µl | previous Rxn |
| 30 µl | DEPC-water |
| 10 µl | 10X JCB Annealing Buffer |
| V$_T$ = 100 µl | |

Heat to 80° C. for 5 minutes, remove heating clock and cool until the temperature reaches 37° C. (for 30 minutes).

EtOH precip with glycogen

Resuspend in 10 µl 0.5×TE (100 ng/µl)

| 2$^{nd}$ Strand Synthesis | | |
|---|---|---|
| 2 µl | 10X T7 Buffer | |
| 3.6 µl | Water | |
| 10 µl | Annealed cDNA (1.1 µg) | |
| 0.5 µl | 20 mM dNTPs | (Epicenter) |
| 0.9 µl | BSA (1 mg/ml) | (NEB) |
| 3 µl | T7 DNA polymerase dilute to (3 Units/µl) | (NEB) |
| V$_T$ = 20 µl | | |

Incubate at 37° C. for 3–5 minutes.

| Transformation | |
|---|---|
| 1 µl (2$^{nd}$) | 2$^{nd}$ strand reactions (11 ng) *diluted (1:5) |
| 40 µl | Electromax DH10B E. coli |
| V$_T$ = 41 µl | |

Electropore the transformation reaction at 1.8 volts.

Add 1 ml of SOC media to the cells and transfer to a culture tube.

Grow for 1 hour at 37° C.

Plate on to LB+100 mcg/ml AMP plates (LARGE) –50 µl & 200 µl.

Grow around 16 hours.

Day Three & Four

Count the colonies and calculate the titer (cfu/µg)

Culturing for Mini-preps

Fill a 96-deep well culture dish with 1 ml of TB with AMP (100 µg/ml).

Pick a single colony using a toothpick and place it into one well. Continue until all wells are inoculated. Remove the toothpicks and cover air pore tape. Grow at least 16 hour overnight (up to 24 hours).

Mini-preps (Qiagen)

Spin down plate at 4000 rpm for 10 minutes (Program #7).

Check for pellet and then pour out media.

Continue following Qiagen 96-well Turbo Mini-prep protocol.

Digests

Use an U-shaped 96-well culture plate for digests.

For 105 Rxn at 15 µl/reaction

| | | |
|---|---|---|
| 210 µl | 2 µl | Buffer #3 |
| | 5 µl | plasmid |
| 1218 µl | 11.6 µl | milli-Q water |
| 63 µl | 0.6 µl | Xho I |
| 63 µl | 0.6 µl | Pst I |
| 21 µl | 0.2 µl | 100X BSA |
| V$_T$ = 1575 µl | V$_T$ = 20 µl | |

Incubate at 37° C. for 2 hours.

Add 3 µl 6× loading dye.

Run on gel at 250 volts for 1.5–2 hours.

Stain gel for 10–15 minutes.

References

Alexander, D. C., McKnight, T. D., & Williams, B. G. (1984). A simplified and efficient vector-primer cDNA cloning system. Gene, 31(1–3), 79–89.

Bellemare, G., Potvin, C., & Bergeron, D. (1991). High-yield method for directional cDNA library construction. Gene, 98, 231–235.

Carninci, P., Kvam, C., Kitamura, A., Ohsumi, T., Okazaka, Y., Itoh, M., Kamiya, M., Shibata, K., Sasaki, N., Izawa, M., Muramatsu, M., Hayashizaki, Y., & Schneider, C. (1996). High-efficiency full-length cDNA cloning by bionylated CAP trapper. Genomics, 37, 327–336.

Carninci, P., Westover, A., Nishiyama, Y., Ohsumi, T., Itoh, M., Nagaoka, S., Sasaki, N., Okazaki, Y., Muramatsu, M., Schneider, C., & Hayashizaki, Y. (1997). High-efficiency selection to full-length cDNA by improved biotinylated cap trapper. DNA Res., 4(1), 61–66.

Edery, I., Chu, L. L., Sonenberg, N., & Pelletier, J. (1995). An efficient strategy to isolate full-length cDNAs based on an mRNA cap retension procedure (CAPture). Mol. Cell. Biol., 15(6), 3363–3371.

Efstratiadis, A., Vournakis, J. N., Donis-Keller, H., Chaconas, G., Dougall, D. K., & Kafatos, F. C. (1977). End labeling of enzymatically decapped mRNA. Nucleic Acids Res., 4(12), 4165–4174.

Fromont-Racine, M., Bertrand, E., Pictet, R., & Grange, T. (1993). A highly sensitive method for mapping the 5' termini of mRNAs. Nucleic Acids Res., 21(7), 1683—1683.

Kato, S., Sekine, S., Oh, S.-W., Kim, N.-S., Umezawa, Y., Abe, N., Yokoyama-Kobayashi, M., & Aoki, T. (1 994). Construction of a human full-length cDNA bank. Gene, 150, 243–250.

Liu, X., & Gorovsky, M. A. (1993). Mapping the 5' and 3' ends of Tetrahymena thermophila mRNA using RNA ligase mediated amplification of cDNA ends (PLM-RACE). Nucleic Acids Res., 21(21), 4954–4960.

Maruyama, K., & Sugano, S. (1994). Oligo-capping: a simple method to replace the cap structure of eukaryotic mRNAs with oligoribonucleotides. Gene, 138, 171–174.

Okayama, H., & Berg, P. (1982). High efficiency cloning of full-length cDNA. Mol. Cell. Biol., 2(2), 161–170.

Shinshi, H., Miwa, M., Kato, K., Noguchi, M., & Matsushima, T. (1976a). A novel phosphodiesterase from cultured tobacco cells. Biochemistry, 15, 2185–2190.

Shinshi, H., Miwa, M., Sugimura, T., Shimotohno, K., & Miura, K.-I. (1976b). Enzyme cleaving the 5'-terminal methylated blocked structure of messenger RNA. FEBS Lett., 65(2), 254–257.

Soares, M. B., Bonaldo, M. F., Jelene, P., Su, L., Lawton, L., & Efstratiadis, A. (1994). Construction and characterization of a normalized cDNA library. Proc. Natl. Acad. Sci. U.S.A., 91(20), 9228–9232.

Tessier, D. C., Brousseau, R., & Vernet, T. (1986). Ligation of single-stranded oligodeoxyribonucleotides by T4 RNA ligase. Analy. Biochem., 158, 171–178.

Yokoyama-Kobayashi, M., & Kota, S. (1993). Rocombinant f1 phage particles can transfect monkey COS-7 cells by DEAE detran method. Biochem. Biophys. Res. Comm., 192, 935–939.

Description of Tables

Table 1 shows the results of making a cDNA library of rabbit globin mRNA using the PAVE method of the present invention.

Table 2 shows the results of making cDNA libraries from a variety of mRNA sources using both "conventional" methods and the PAVE method of the present invention. The "conventional" method employed a kit obtained from GIBCO/BRL and utilized a 3' oligo-dT primer and SauI adaptors.

Table 3 shows a number of parameters of the T4 RNA ligase reaction that may be modified to obtain optimal efficiency of the reaction. The most preferred reaction conditions include performing the reaction at room temperature overnight (or 16 hours); using an acceptor/donor ratio that is the same as that obtained from reacting 2 μg mRNA (average size 1.5 kb) with 175 pmoles of a 27-residue RNA tag; and performing the reaction in RNAse-free Tris MgCl$_2$ buffer with tRNA, DTT, and 5.8 nM ATP added.

TABLE 1

Analysis of cDNA library made from rabbit globin mRNA

|  | Number of Colonies | Percentage |
|---|---|---|
| Total Positives[a] | 385 | 100% |
| Full-length[b] | 292 | 75.8% |
| 3'-only[c] | 75 | 19.5% |
| 5'-only[d] | 10 | 4.7% |

[a]Duplicate filters were lifted from one plate and hybridized to two labeled oligonucleotide probes complementary to 5' and 3' ends of rabbit β-globin mRNA. The total positives were counted.
[b]Full-length clones were double positives to 5' and 3' probes.
[c]Clonex hybridized only to 3'-end probes.
[d]Clonex hybridized only to 5'-end probes.

Definitions of Data Table Categories

Type=Two types of cDNA libraries were analyzed in this study. "Conventional" refers to libraries that are constructed with a 3' oligo dt primer. "PAVE" refers to 5'-directed cDNA library construction technology.

100% FL=Represents the percentage of clones that contain 100% or greater 5' sequence relative to their respective GenBank record.

98.5% FL=Represents the percentage of clones that contain 98.5% or greater 5' sequence relative to their respective GenBank record.

Median % FL=Represents the median full-length value of all the clones analyzed.

Correct Size=Represents the percentage of clones that were 100% FL or greater than size matched after restriction digestion analysis.

Average FL Size=Represents the average size of the clones that were 100% full-length based on restriction enzyme digestion analysis.

TABLE 3

Optimization of RNA-RNA ligation by T4 RNA ligase

| | |
|---|---|
| 1. Effect of Temperature: | 4° C., O/N; 16° C., O/N; Room Temperature, O/N; 37° C., O/N; 37° C., 3 hrs. |
| 2. Time Courses at Suitable Temperature: | 0.5, 2, 4, 8, 16, 24 hrs |
| 3. Effect of Denaturants: | DMSO: 10%, 20%, 30%, 40% Urea: 0.5M, 1M, 2M, 3M, 4M Formamide: 5%, 10%, 20%, 40% |
| 4. Effect of Accepter/Donor Ratio: | 1, 10, 20, 50, 100, 200 |
| 5. Effect of PEG: | 5%, 10%, 15%, 20%, 25% |
| 6. Effect of Buffers (?): | Glycylglycine, HEPES or Tris |
| 7. Effect of Inorganic Pyrophosphotase | (Ppi is inhibitory, but Pi is not) |
| 8. Effect of HCC (hexamine colbalt chloride): | 0.5 mM, 1 mM, 2 mM, 5 mM, 10 mM |
| 9. Effect of Single-Stranded RNA Binding Proteins | (i.e., T4 gene 32 protein) |

TABLE 2

CDNA Library Comparison

| Type | Tissue/Cells | 100% FL | 98.5% FL | # Sequenced | #mRNA cds | % Flipped | Median % FL | Correct size | Average FL Size |
|---|---|---|---|---|---|---|---|---|---|
| Conventional | HT1080 | 42% | 48% | 342 | 91 | 1.3% | 95% | 78% | 601 bp |
| Conventional | Thymus | 19% | 23% | 4263 | 663 | 0.5% | 58% | 58% | 2003 bp |
| Conventional | WERI-RB | 23% | 26% | 4021 | 715 | 0.3% | 63% | 50% | 1275 bp |
| Pave | HT1080 | 64% | 67% | 206 | 49 | 0.1% | 93% | 81% | 993 bp |
| Pave | Thymus | 50% | 50% | 40 | 20 | 0.0% | 98% | N/A | 562 bp |
| Pave | WERI-RB | 34% | 38% | 278 | 63 | 0.0% | 90% | N/A | 956 bp |

What is claimed is:

1. A method for producing a cDNA library comprising the steps of:
   a) isolating a crude mRNA pool from a cell culture;
   b) labeling only full-length mRNA in the pool with a biotinylated tag comprising SEQ ID NO: 8; and
   c) contacting the labeled full-length mRNA, resulting from step b), with a vector wherein said vector comprises a cDNA primer.

* * * * *

SEQUENCE LISTING

<160> NUMBER OF SEQ ID NOS: 8

<210> SEQ ID NO 1
<211> LENGTH: 50
<212> TYPE: DNA
<213> ORGANISM: Artificial Sequence
<220> FEATURE:
<223> OTHER INFORMATION: LINKER FOR PREPARATION OF VECTOR-PRIMER-EXAMPLE
      1

<400> SEQUENCE: 1
aattcgagtg aacactcgag ctcactagtg accagctgat gcgcctcaaa            50

<210> SEQ ID NO 2
<211> LENGTH: 19
<212> TYPE: DNA
<213> ORGANISM: Artificial Sequence
<220> FEATURE:
<223> OTHER INFORMATION: LINKER FOR PREPARATION OF VECTOR-PRIMER-EXAMPLE
      1

<400> SEQUENCE: 2
gctcacttgt gagctcgag                                              19

<210> SEQ ID NO 3
<211> LENGTH: 23
<212> TYPE: DNA
<213> ORGANISM: Artificial Sequence
<220> FEATURE:
<223> OTHER INFORMATION: LINKER FOR PREPARATION OF VECTOR-PRIMER-EXAMPLE
      1

<400> SEQUENCE: 3
ctaatctgat ccgctagtgg tac                                         23

<210> SEQ ID NO 4
<211> LENGTH: 57
<212> TYPE: DNA
<213> ORGANISM: Artificial Sequence
<220> FEATURE:
<223> OTHER INFORMATION: LINKER FOR PREPARATION OF VECTOR-PRIMER-EXAMPLE
      1

<400> SEQUENCE: 4
tttttttttt tttttttttt tttttttttt gattagacta ggcgatcacc atgagct    57

<210> SEQ ID NO 5
<211> LENGTH: 21
<212> TYPE: DNA
<213> ORGANISM: Artificial Sequence
<220> FEATURE:
<223> OTHER INFORMATION: DNA TAG CREATED TO ASSESS EFICIENCY OF RNA TAG-
      EXAMPLE 2

<400> SEQUENCE: 5
gaggcgtatc agctggtcac t                                           21

<210> SEQ ID NO 6
<211> LENGTH: 5462
<212> TYPE: DNA
<213> ORGANISM: Artificial Sequence
<220> FEATURE:
<223> OTHER INFORMATION: DERIVATIVE OF E.COLI PUC19

<400> SEQUENCE: 6

-continued

| | |
|---|---|
| aagcttttg caaaagccta ggcctccaaa aaagcctcct cactacttct ggaatagctc | 60 |
| agaggccgag gcggcctcgg cctctgcata aataaaaaaa attagtcagc catgggcgg | 120 |
| agaatgggcg gaactgggcg gagttagggg cgggatgggc ggagttaggg gcggactat | 180 |
| ggttgctgac taattgagat gcatgctttg catacttctg cctgctgggg agcctgggga | 240 |
| ctttccacac ctggttgctg actaattgag atgcatgctt tgcatacttc tgcctgctgg | 300 |
| ggagcctggg gactttccac accctaactg acacacattc cacaggatcc ggtcgcgcga | 360 |
| atttcgagcg gtgttccgcg gtcctcctcg tatagaaact cggaccactc tgagacgaag | 420 |
| gctcgcgtcc aggccagcac gaaggaggct aagtgggagg ggtagcggtc gttgtccact | 480 |
| aggggtcca ctcgctccag ggtgtgaaga cacatgtcgc cctcttcggc atcaaggaag | 540 |
| gtgattggtt tataggtgta ggccacgtga ccgggtgttc ctgaaggggg gctataaaag | 600 |
| ggggtggggg cgcgttcgtc ctcactctct tccgcatcgc tgtctgcgag gccagctgt | 660 |
| tgggctcgcg gttgaggaca aactcttcgc ggtctttcca gtactcttgg atcggaaacc | 720 |
| cgtcggcctc cgaacggtac tccgccaccg agggacctga gcgagtccgc atcgaccgga | 780 |
| tcggaaaacc tctcgactgt tggggtgagt actccctctc aaaagcgggc atgacttctg | 840 |
| cgctaagatt gtcagtttcc aaaaacgagg aggatttgat attcacctgg cccgcggtga | 900 |
| tgcctttgag ggtggccgcg tccatctggt cagaaaagac aatctttttg ttgtcaagct | 960 |
| tgaggtgtgg caggcttgag atctggccat acacttgagt gacaatgaca tccactttgc | 1020 |
| ctttctctcc acaggtgtcc actcccaggt ccaactgcag gccggcctct aatacgactc | 1080 |
| actatagggc gcgcctgaat tcgatatctt aagcccgggt acgtcgacgc ggccgcgcga | 1140 |
| tcgcccttta gtgagggtta attaactcga gtctagaccg gggccgcaat tctaacgtta | 1200 |
| ctggccgaag ccgcttggaa taaggccggt gtgcgtttgt ctatatgtta ttttccacca | 1260 |
| tattgccgtc ttttggcaat gtgagggccc ggaaacctgg ccctgtcttc ttgacgagca | 1320 |
| ttcctagggg tctttcccct ctcgccaaag gaatgcaagg tctgttgaat gtcgtgaagg | 1380 |
| aagcagttcc tctggaagct tcttgaagac aaacaacgtc tgtagcgacc ctttgcaggc | 1440 |
| agcggaaccc cccacctggc gacaggtgcc tctgcggcca aaagccacgt gtataagata | 1500 |
| cacctgcaaa ggcggcacaa ccccagtgcc acgttgtgag ttggatagtt gtggaaagag | 1560 |
| tcaaatggct ctcctcaagc gtattcaaca agggctgaa ggatgcccag aagtacccc | 1620 |
| attgtatggg atctgatctg gggcctcggt gcacatgctt tacatgtgtt tagtcgaggt | 1680 |
| taaaaaacgt ctaggccccc cgaaccacgg ggacgtggtt ttcctttgaa aaacacgatg | 1740 |
| ataatattgc cacaaccatg gttcgaccat tgaactgcat cgtcgccgtg tcccaaaata | 1800 |
| tggggattgg caagaacgga gacctaccct ggcctccgct caggaacgag ttcaagtact | 1860 |
| tccaaagaat gaccacaacc tcttcagtgg aaggtaaaca gaatctggtg attatgggta | 1920 |
| ggaaaacctg gttctccatt cctgagaaga atcgaccttt aaaggacaga attaatatag | 1980 |
| ttctcagtag agaactcaaa gaaccaccac gaggagctca ttttcttgcc aaaagtttgg | 2040 |
| atgatgcctt aagacttatt gaacaaccgg aattggcaag taaagtagac atggtttgga | 2100 |
| tagtcggagg cagttctgtt taccaggaag ccatgaatca accaggccac ctcagactct | 2160 |
| ttgtgacaag gatcatgcag gaatttgaaa gtgacacgtt tttcccagaa attgatttgg | 2220 |
| ggaaatataa acttctccca gaatacccag gcgtcctctc tgaggtccag gaggaaaaag | 2280 |
| gcatcaagta taagtttgaa gtctacgaga agaaagacta acaggaagat gctttcaagt | 2340 |
| tctctgctcc cctcctaaag ctatgcattt tttataagac catgggactt ttgctggctt | 2400 |

```
tagatcataa tcagccatac cacatttgta gaggttttac ttgctttaaa aaacctccca    2460
cacctccccc tgaacctgaa acataaaatg aatgcaattg ttgttgttaa cttgtttatt    2520
gcagcttata atggttacaa ataaagcaat agcatcacaa atttcacaaa taaagcattt    2580
ttttcactgc attctagttg tggtttgtcc aaactcatca atgtatctta tcatgtctgg    2640
atccccggcc aacggtctgg tgaccggct gcgagagctc ggtgtacctg agacgcgagt    2700
aagcccttga gtcaaagacg tagtcgttgc aagtccgcac caggtactga tcatcgatgc    2760
tagaccgtgc aaaaggagag cctgtaagcg ggcactcttc cgtggtctgg tggataaatt    2820
cgcaagggta tcatggcgga cgaccggggt tcgaaccccg gatccggccg tccgccgtga    2880
tccatccggt taccgcccgc gtgtcgaacc caggtgtgcg acgtcagaca acgggggagc    2940
gctccttttg gcttccttcc aggcgcggcg gctgctgcgc tagcttttttt ggcgagctcg    3000 aattaattct gcattaatga atcggccaac gcgcggggag aggcggtttg cgtattgggc    3060
gctcttccgc ttcctcgctc actgactcgc tgcgctcggt cgttcggctg cggcgagcgg    3120
tatcagctca ctcaaaggcg gtaatacggt tatccacaga atcaggggat aacgcaggaa    3180
agaacatgtg agcaaaaggc cagcaaaagg ccaggaaccg taaaaaggcc gcgttgctgg    3240
cgttttccca taggctccgc cccctgacga gcatcacaa aaatcgacgc tcaagtcaga    3300
ggtggcgaaa cccgacagga ctataaagat accaggcgtt tccccctgga agctccctcg    3360
tgcgctctcc tgttccgacc ctgccgctta ccggatacct gtccgccttt ctcccttcgg    3420
gaagcgtggc gctttctcaa tgctcacgct gtaggtatct cagttcggtg taggtcgttc    3480
gctccaagct gggctgtgtg cacgaacccc cgttcagcc cgaccgctgc gccttatccg    3540
gtaactatcg tcttgagtcc aacccggtaa gacacgactt atcgccactg gcagcagcca    3600
ctggtaacag gattagcaga gcgaggtatg taggcggtgc tacagagttc ttgaagtggt    3660
ggcctaacta cggctacact agaaggacag tatttggtat ctgcgctctg ctgaagccag    3720
ttaccttcgg aaaaagagtt ggtagctctt gatccggcaa acaaaccacc gctggtagcg    3780
gtggtttttt tgtttgcaag cagcagatta cgcgcagaaa aaaaggatct caagaagatc    3840
ctttgatctt ttctacgggg tctgacgctc agtggaacga aaactcacgt taagggattt    3900
tggtcatgag attatcaaaa aggatcttca cctagatcct tttaaattaa aaatgaagtt    3960
ttaaatcaat ctaaagtata tatgagtaaa cttggtctga cagttaccaa tgcttaatca    4020
gtgaggcacc tatctcagcg atctgtctat ttcgttcatc catagttgcc tgactccccg    4080
tcgtgtagat aactacgata cgggagggct taccatctgg ccccagtgct gcaatgatac    4140
cgcgagaccc acgctcaccg gctccagatt tatcagcaat aaaccagcca gccggaaggg    4200
ccgagcgcag aagtggtcct gcaactttat ccgcctccat ccagtctatt aattgttgcc    4260
gggaagctag agtaagtagt tcgccagtta atagtttgcg caacgttgtt gccattgcta    4320
caggcatcgt ggtgtcacgc tcgtcgtttg gtatggcttc attcagctcc ggttcccaac    4380
gatcaaggcg agttacatga tcccccatgt tgtgcaaaaa agcggttagc tccttcggtc    4440
ctccgatcgt tgtcagaagt aagttggccg cagtgttatc actcatggtt atggcagcac    4500
tgcataattc tcttactgtc atgccatccg taagatgctt ttctgtgact ggtgagtact    4560
caaccaagtc attctgagaa tagtgtatgc ggcgaccgag ttgctcttgc ccggcgtcaa    4620
tacgggataa taccgcgcca catagcagaa ctttaaaagt gctcatcatt ggaaaacgtt    4680
cttcggggcg aaaactctca aggatcttac cgctgttgag atccagttcg atgtaaccca    4740
```

| | |
|---|---|
| ctcgtgcacc caactgatct tcagcatctt ttactttcac cagcgtttct gggtgagcaa | 4800 |
| aaacaggaag gcaaaatgcc gcaaaaaagg gaataagggc gacacggaaa tgttgaatac | 4860 |
| tcatactctt cctttttcaa tattattgaa gcatttatca gggttattgt ctcatgagcg | 4920 |
| gatacatatt tgaatgtatt tagaaaaata acaaataggg gttccgcgc acatttcccc | 4980 |
| gaaaagtgcc acctgacgtc taagaaacca ttattatcat gacattaacc tataaaaata | 5040 |
| ggcgtatcac gaggccctt cgtctcgcgc gtttcggtga tgacggtgaa aacctctgac | 5100 |
| acatgcagct cccggagacg gtcacagctt gtctgtaagc ggatgccggg agcagacaag | 5160 |
| cccgtcaggg cgcgtcagcg ggtgttggcg ggtgtcgggg ctggcttaac tatgcggcat | 5220 |
| cagagcagat tgtactgaga gtgcaccata tgcggtgtga ataccgcac agatgcgtaa | 5280 |
| ggagaaaata ccgcatcagg cgccattcgc cattcaggct gcgcaactgt tgggaagggc | 5340 |
| gatcggtgcg ggcctcttcg ctattacgcc agctggcgaa aggggatgt gctgcaaggc | 5400 |
| gattaagttg ggtaacgcca gggttttccc agtcacgacg ttgtaaaacg acggccagtg | 5460 |
| cc | 5462 |

<210> SEQ ID NO 7
<211> LENGTH: 5374
<212> TYPE: DNA
<213> ORGANISM: Artificial Sequence
<220> FEATURE:
<223> OTHER INFORMATION: DERIVATIVE OF E.COLI PUC19

<400> SEQUENCE: 7

| | |
|---|---|
| aagcttttg caaaagccta ggcctccaaa aaagcctcct cactacttct ggaatagctc | 60 |
| agaggccgag gcggcctcgg cctctgcata ataaaaaaa attagtcagc catggggcgg | 120 |
| agaatgggcg gaactgggcg gagttagggg cgggatgggc ggagttaggg gcgggactat | 180 |
| ggttgctgac taattgagat gcatgctttg catacttctg cctgctgggg agcctgggga | 240 |
| cttccacac ctggttgctg actaattgag atgcatgctt tgcatacttc tgcctgctgg | 300 |
| ggagcctggg gactttccac accctaactg acacacattc cacaggatcc ggtcgcgcga | 360 |
| atttcgagcg gtgttccgcg gtcctcctcg tatagaaact cggaccactc tgagacgaag | 420 |
| gctcgcgtcc aggccagcac gaaggaggct aagtgggagg gtagcggtc gttgtccact | 480 |
| agggggtcca ctcgctccag ggtgtgaaga cacatgtcgc cctcttcggc atcaaggaag | 540 |
| gtgattggtt tataggtgta ggccacgtga ccggtgttc ctgaaggggg gctataaaag | 600 |
| ggggtggggg cgcgttcgtc ctcactctct tccgcatcgc tgtctgcgag ggccagctgt | 660 |
| tgggctcgcg gttgaggaca aactcttcgc ggtctttcca gtactcttgg atcggaaacc | 720 |
| cgtcggcctc cgaacggtac tccgccaccg agggacctga gcgagtccgc atcgaccgga | 780 |
| tcggaaaacc tctcgactgt tggggtgagt actccctctc aaaagcgggc atgacttctg | 840 |
| cgctaagatt gtcagtttcc aaaaacgagg aggatttgat attcacctgg cccgcggtga | 900 |
| tgcctttgag ggtggccgcg tccatctggt cagaaaagac aatctttttg ttgtcaagct | 960 |
| tgaggtgtgg caggcttgag atctggccat acacttgagt gacaatgaca tccactttgc | 1020 |
| ctttctctcc acaggtgtcc actcccaggt ccaactgcag acttcgaatt ctactgactc | 1080 |
| gagactctat tgcggccgca attctaacgt tactggccga agccgcttgg aataaggccg | 1140 |
| gtgtgcgttt gtctatatgt tattttccac catattgccg tcttttggca atgtgagggc | 1200 |
| ccggaaacct ggccctgtct tcttgacgag cattcctagg ggtctttccc ctctcgccaa | 1260 |
| aggaatgcaa ggtctgttga atgtcgtgaa ggaagcagtt cctctggaag cttcttgaag | 1320 |

```
acaaacaacg tctgtagcga ccctttgcag gcagcggaac cccccacctg gcgacaggtg   1380
cctctgcggc caaaagccac gtgtataaga tacacctgca aaggcggcac aaccccagtg   1440
ccacgttgtg agttggatag ttgtggaaag agtcaaatgg ctctcctcaa gcgtattcaa   1500 caagggctg aaggatgccc agaaggtacc ccattgtatg ggatctgatc tggggcctcg   1560
gtgcacatgc tttacatgtg tttagtcgag gttaaaaaac gtctaggccc cccgaaccac   1620
ggggacgtgg ttttcctttg aaaaacacga tgataatatt gccacaacca tggttcgacc   1680
attgaactgc atcgtcgccg tgtcccaaaa tatgggggatt ggcaagaacg gagacctacc   1740
ctggcctccg ctcaggaacg agttcaagta cttccaaaga atgaccacaa cctcttcagt   1800
ggaaggtaaa cagaatctgg tgattatggg taggaaaacc tggttctcca ttcctgagaa   1860
gaatcgacct ttaaaggaca gaattaatat agttctcagt agagaactca agaaccacc   1920 acgaggagct cattttcttg ccaaaagttt ggatgatgcc ttaagactta ttgaacaacc   1980
ggaattggca agtaaagtag acatggtttg gatagtcgga ggcagttctg tttaccagga   2040
agccatgaat caaccaggcc acctcagact ctttgtgaca aggatcatgc aggaatttga   2100
aagtgacacg tttttcccag aaattgattt ggggaaatat aaacttctcc cagaataccc   2160
aggcgtcctc tctgaggtcc aggaggaaaa aggcatcaag tataagtttg aagtctacga   2220
gaagaaagac taacaggaag atgctttcaa gttctctgct cccctcctaa agctatgcat   2280
tttttataag accatgggac ttttgctggc tttagatcat aatcagccat accacatttg   2340
tagaggtttt acttgcttta aaaaacctcc cacacctccc cctgaacctg aaacataaaa   2400
tgaatgcaat tgttgttgtt aacttgttta ttgcagctta taatggttac aaataaagca   2460
atagcatcac aaatttcaca aataaagcat tttttttcact gcattctagt tgtggtttgt   2520
ccaaactcat caatgtatct tatcatgtct ggatccccgg ccaacggtct ggtgacccgg   2580
ctgcgagagc tcggtgtacc tgagacgcga gtaagcccct gagtcaaaga cgtagtcgtt   2640
gcaagtccgc accaggtact gatcatcgat gctagaccgt gcaaaaggag agcctgtaag   2700
cgggcactct tccgtggtct ggtggataaa ttcgcaaggg tatcatggcg gacgaccggg   2760
gttcgaaccc cggatccggc cgtccgccgt gatccatccg gttaccgccc gcgtgtcgaa   2820
cccaggtgtg cgacgtcaga caacggggga gcgctccttt tggcttcctt ccaggcgcgg   2880
cggctgctgc gctagctttt ttggcgagct cgaattaatt ctgcattaat gaatcggcca   2940
acgcgcgggg agaggcggtt tgcgtattgg gcgctcttcc gcttcctcgc tcactgactc   3000
gctgcgctcg tcgttcggc tgcggcgagc ggtatcagct cactcaaagg cggtaatacg   3060
gttatccaca gaatcagggg ataacgcagg aaagaacatg tgagcaaaag gccagcaaaa   3120
ggccaggaac cgtaaaaagg ccgcgttgct ggcgtttttc cataggctcc gcccccctga   3180
cgagcatcac aaaaatcgac gctcaagtca gaggtggcga aacccgacag gactataaag   3240
ataccaggcg tttccccctg gaagctccct cgtgcgctct cctgttccga ccctgccgct   3300
taccggatac ctgtccgcct ttctcccttc gggaagcgtg gcgctttctc aatgctcacg   3360
ctgtaggtat ctcagttcgg tgtaggtcgt tcgctccaag ctgggctgtg tgcacgaacc   3420
ccccgttcag cccgaccgct gcgccttatc cggtaactat cgtcttgagt ccaacccggt   3480
aagacacgac ttatcgccac tggcagcagc cactggtaac aggattagca gagcgaggta   3540
tgtaggcggt gctacagagt tcttgaagtg gtggcctaac tacggctaca ctagaaggac   3600
agtatttggt atctgcgctc tgctgaagcc agttaccttc ggaaaaagag ttggtagctc   3660
```

-continued

```
ttgatccggc aaacaaacca ccgctggtag cggtggtttt tttgtttgca agcagcagat    3720
tacgcgcaga aaaaaaggat ctcaagaaga tcctttgatc ttttctacgg ggtctgacgc    3780
tcagtggaac gaaaactcac gttaagggat tttggtcatg agattatcaa aaaggatctt    3840
cacctagatc cttttaaatt aaaaatgaag ttttaaatca atctaaagta tatatgagta    3900
aacttggtct gacagttacc aatgcttaat cagtgaggca cctatctcag cgatctgtct    3960
atttcgttca tccatagttg cctgactccc cgtcgtgtag ataactacga tacgggaggg    4020
cttaccatct ggccccagtg ctgcaatgat accgcgagac ccacgctcac cggctccaga    4080
tttatcagca ataaaccagc cagccggaag ggccgagcgc agaagtggtc ctgcaacttt    4140
atccgcctcc atccagtcta ttaattgttg ccgggaagct agagtaagta gttcgccagt    4200
taatagtttg cgcaacgttg ttgccattgc tacaggcatc gtggtgtcac gctcgtcgtt    4260
tggtatggct tcattcagct ccggttccca acgatcaagg cgagttacat gatcccccat    4320
gttgtgcaaa aaagcggtta gctccttcgg tcctccgatc gttgtcagaa gtaagttggc    4380
cgcagtgtta tcactcatgg ttatggcagc actgcataat tctcttactg tcatgccatc    4440
cgtaagatgc ttttctgtga ctggtgagta ctcaaccaag tcattctgag aatagtgtat    4500
gcggcgaccg agttgctctt gcccggcgtc aatacgggat aataccgcgc cacatagcag    4560
aactttaaaa gtgctcatca ttggaaaacg ttcttcgggg cgaaaactct caaggatctt    4620
accgctgttg agatccagtt cgatgtaacc cactcgtgca cccaactgat cttcagcatc    4680
ttttactttc accagcgttt ctgggtgagc aaaaacagga aggcaaaatg ccgcaaaaaa    4740
gggaataagg gcgacacgga aatgttgaat actcatactc ttcctttttc aatattattg    4800
aagcatttat cagggttatt gtctcatgag cggatacata tttgaatgta tttagaaaaa    4860
taaacaaata ggggttccgc gcacatttcc ccgaaaagtg ccacctgacg tctaagaaac    4920
cattattatc atgacattaa cctataaaaa taggcgtatc acgaggccct ttcgtctcgc    4980
gcgtttcggt gatgacggtg aaaacctctg acacatgcag ctcccggaga cggtcacagc    5040
ttgtctgtaa gcggatgccg ggagcagaca agcccgtcag ggcgcgtcag cgggtgttgg    5100
cgggtgtcgg ggctggctta actatgcggc atcagagcag attgtactga gagtgcacca    5160
tatgcggtgt gaaataccgc acagatgcgt aaggagaaaa taccgcatca ggcgccattc    5220
gccattcagg ctgcgcaact gttgggaagg gcgatcggtg cgggcctctt cgctattacg    5280
ccagctggcg aaagggggat gtgctgcaag gcgattaagt tgggtaacgc cagggttttc    5340
ccagtcacga cgttgtaaaa cgacggccag tgcc                                5374
```

<210> SEQ ID NO 8
<211> LENGTH: 27
<212> TYPE: RNA
<213> ORGANISM: Artificial Sequence
<220> FEATURE:
<223> OTHER INFORMATION: SYNTHETIC RNA CREATED FOR USE AS DESCRIBED IN
      EXAMPLE 2

<400> SEQUENCE: 8
acuagugacc agcugauacg ccucaaa                                            27